United States Patent [19]

Dyson et al.

[11] Patent Number: 5,274,108
[45] Date of Patent: Dec. 28, 1993

[54] PROCESS FOR PREPARING 1,3-DIOXOLANE DERIVATIVES

[75] Inventors: Norman H. Dyson, Palo Alto; John O. Gardner, Los Altos; Anthony Prince; Denis J. Kertesz, both of Mountain View, all of Calif.

[73] Assignee: Syntex (U.S.A.) Inc., Palo Alto, Calif.

[21] Appl. No.: 993,789

[22] Filed: Dec. 21, 1992

Related U.S. Application Data

[62] Division of Ser. No. 900,568, Jun. 18, 1992, Pat. No. 5,208,331.

[51] Int. Cl.$^5$ .................. C07D 405/00; C07D 405/14
[52] U.S. Cl. .............................. 548/311.1; 548/314.7
[58] Field of Search ........................ 548/311.1, 314.7

[56] References Cited

U.S. PATENT DOCUMENTS

| | | | |
|---|---|---|---|
| 3,936,470 | 2/1976 | Heeres | 548/311.1 |
| 4,078,071 | 3/1978 | Walker et al. | 548/311.1 |
| 4,144,346 | 3/1979 | Heeres et al. | 548/311.1 |
| 4,209,447 | 6/1980 | Heeres | 548/311.1 |
| 4,321,272 | 3/1982 | Walker et al. | 548/311.1 |
| 4,335,125 | 6/1982 | Heeres et al. | 548/311.1 |
| 4,359,475 | 11/1982 | Walker et al. | 545/311.1 |
| 4,375,474 | 3/1983 | Walker | 548/311.1 X |
| 4,490,540 | 12/1984 | Heeres et al. | 548/311.1 |
| 4,518,607 | 5/1985 | Walker et al. | 548/311.1 |
| 4,940,799 | 7/1990 | Aebi et al. | 548/311.1 |
| 5,158,949 | 10/1992 | Walker et al. | 514/227.8 |
| 5,208,331 | 5/1993 | Dyson et al. | 544/60 |

FOREIGN PATENT DOCUMENTS

| | | | |
|---|---|---|---|
| 1187085 | 5/1985 | Canada | 548/311.1 |
| 0052905 | 6/1982 | European Pat. Off. | 548/311.1 |
| 0130077 | 1/1985 | European Pat. Off. | 548/311.1 |
| 0335446 | 10/1989 | European Pat. Off. | 548/311.1 |
| 1364395 | 8/1974 | United Kingdom | 548/311.1 |
| 2027701 | 2/1980 | United Kingdom | 548/311.1 |

OTHER PUBLICATIONS

*Journal of Lipid Research* (1988), vol. 29, pp. 43-51.
*J. Steroid Biochem.* (1987), vol. 28, No. 5, pp. 521-531.
*J. Androl.* (1987), vol. 8, pp. 230-237.

(List continued on next page.)

*Primary Examiner*—Floyd D. Higel
*Attorney, Agent, or Firm*—Carol J. Roth; Derek P. Freyberg; Alan M. Krupiner

[57] ABSTRACT

This invention provides an improved process for the preparation of compounds of formula (I):

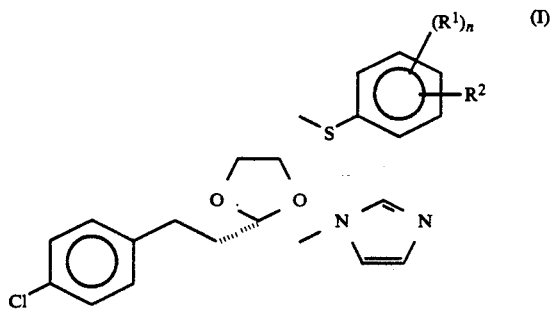

wherein:
n is 0, 1 or 2;
each $R^1$ is independently halo or lower alkyl;
$R^2$ is nitro or —$N(R^3)R^4$ where
  $R^3$ is hydrogen or lower alkyl;
  $R^4$ is hydrogen, lower alkyl, lower alkylsulfonyl or —C(Y)$R^5$ where Y is oxygen or sulfur and $R^5$ is hydrogen, lower alkyl, lower alkoxy or —N($R^6$)$R^7$ where $R^6$ is hydrogen or lower alkyl and $R^7$ is hydrogen, lower alkyl or lower alkoxycarbonyl; or
  $R^3$ and $R^4$ together with N is pyrrolidino, piperidino, morpholino, thiomorpholino or piperazino, wherein the piperazino is optionally substituted at the 4-position by —C(O)$R^8$ where $R^8$ is hydrogen, lower alkyl, lower alkoxy or amino;

or pharmaceutically acceptable salts thereof. These compounds are useful in treating disease-states characterized by hypercholesterolemia.

10 Claims, No Drawings

OTHER PUBLICATIONS

*Am. J. Trop. Med. Hyg.* (1987), vol. 37, No. 2, pp. 308–313.
*The American Journal of Medicine* (1986), vol. 80, pp. 616–621.
*The Journal of Pharmacology and Experimental Therapeutics* (1986), vol. 238, No. 3, pp. 905–911.
*Eur. J. Clin. Pharmacol.* (1985), vol. 29, pp. 241–245.
*Male Contraception: Advances and Future Prospectus* (1985), Chap. 25, pp. 271–292.
*Arch. Intern. Med.* (1982), vol. 142, pp. 2137–2140.
*Pesticide Chemistry: Human Welfare and the Environment*, Proc. Int. *Congr. Pestic. Chem.* 5th (1983), vol. 1, pp. 303–308.
Gadher et al., *Pesticide Biochemistry and Physiology* (1983), vol. 19, pp. 1–10.
Tidwell, *Synthesis* (1990), pp. 857–870.
Parikh et al., *Journal of American Chemical Society* (1967), vol. 89, No. 21, pp. 5505–5507.
Gilbert, *Chem. Rev.* (1962), vol. 62, pp. 550–555.

PROCESS FOR PREPARING 1,3-DIOXOLANE DERIVATIVES

This is a division of pending application Ser. No. 07/900,568, filed Jun. 18, 1992, incorporated herein by reference, and now U.S. Pat. No. 5,208,331.

FIELD OF THE INVENTION

This invention relates to an improved process for the preparation and separation of individual stereoisomers of certain 1,3-dioxolane derivatives useful in treating mammals having disease-states characterized by hypercholesterolemia.

BACKGROUND OF THE INVENTION

Processes for the preparation of compounds of formula (I):

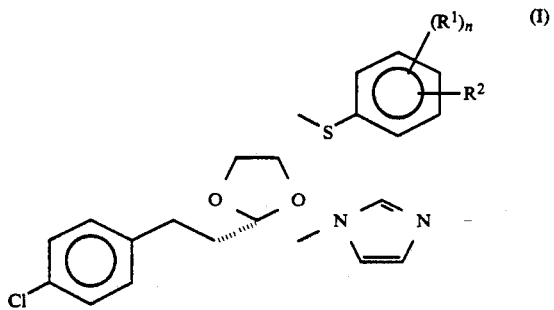

wherein
n is 0, 1 or 2;
each $R^1$ is independently halo or lower alkyl;
$R^2$ is nitro or $-N(R^3)R^4$ where
  $R^3$ is hydrogen or lower alkyl;
  $R^4$ is hydrogen, lower alkyl, lower alkylsulfonyl or $-C(Y)R^5$ where Y is oxygen or sulfur and $R^5$ is hydrogen, lower alkyl, lower alkoxy or $-N(R^6)R^7$ where $R^6$ is hydrogen or lower alkyl and $R^7$ is hydrogen, lower alkyl or lower alkoxycarbonyl; or
  $R^3$ and $R^4$ together with N is pyrrolidino, piperidino, morpholino, thiomorpholino or piperazino, wherein the piperazino is optionally substituted at the 4-position by $-C(O)R^8$ where $R^8$ is hydrogen, lower alkyl, lower alkoxy or amino;
or a pharmaceutically acceptable salt thereof; are described, inter alia, in co-pending U.S. patent application Ser. No. 07/633,599, filed Dec. 20, 1990, the disclosure of which is incorporated in full herein by reference.

The compounds of formula (I), including their pharmaceutically acceptable salts, and the compositions containing them, inhibit cholesterol synthesis and are therefore useful in treating disease-states characterized by hypercholesterolemia. In particular, compounds of formula (I) inhibit cholesterol synthesis by inhibiting lanosterol 14α-demethylase, a cytochrome P-450 enzyme. Compounds of formula (I) are also more effective in inhibiting lanosterol 14α-demethylase than they are in inhibiting other cytochrome P-450 enzymes, for example, the cytochrome P-450 enzymes which contribute to gonadal and adrenal steroidogenesis and cholesterol degradation. Thus, the compounds of formula (I) are useful in treating disease-states characterized by hypercholesterolemia with minimum effect on the physiological functions of key cytochrome P-450 enzymes.

SUMMARY OF THE INVENTION

In general, the present invention is directed to an improved and efficient process for the preparation of single stereoisomers of compounds of formula (I) and their pharmaceutically acceptable salts. In the previously disclosed preparation of the compounds of formula (I) the individual stereoisomers were separated by the conventional method of flash chromatography, e.g., elution with 0.1% NH$_4$OH and 5% methanol, which was gradually changed to a solution of 0.2% NH$_4$OH and 10% methanol, in a 3:3:2 mixture of ethyl acetate, methylene chloride and hexane. One of the advantages that the present invention has over the previously disclosed preparation of the compounds of formula (I) is the ease at which intermediates of compounds of formula (I) are separated out from a mixture of stereoisomers. This is accomplished through the crystallization of the nitrate salts of the undesired stereoisomers, i.e., the trans-stereoisomers which correspond to the desired cis-stereoisomers. Upon formation, the nitrate salts of the undesired trans-stereoisomers precipitate out from the reaction mixture leaving the desired cis-stereoisomers in the mother liquor for further processing.

The process of the instant invention also allows for the undesired trans-stereoisomers to be recycled back into the process described herein. This is accomplished through the re-equilibration of the undesired trans-stereoisomers to a mixture of the trans- and cis-stereoisomers. This mixture can then be further treated as described above to separate out the desired cis-stereoisomers from the undesired trans-stereoisomers.

Accordingly, the present invention has several different aspects to it. In one aspect, the present invention provides a process for the preparation of compounds of formula (I):

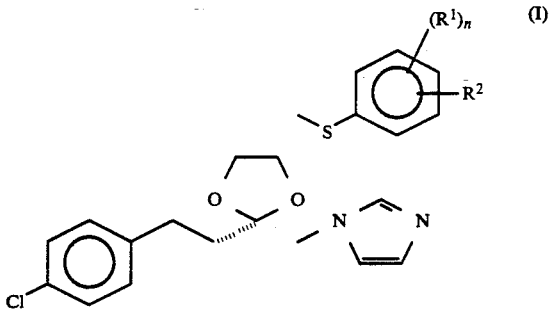

wherein:
n is 0, 1 or 2;
each $R^1$ is independently halo or lower alkyl;
$R^2$ is nitro or $-N(R^3)R^4$ where
  $R^3$ is hydrogen or lower alkyl;
  $R^4$ is hydrogen, lower alkyl, lower alkylsulfonyl or $-C(Y)R^5$ where Y is oxygen or sulfur and $R^5$ is hydrogen, lower alkyl, lower alkoxy or $-N(R^6)R^7$ where $R^6$ is hydrogen or lower alkyl and $R^7$ is hydrogen, lower alkyl or lower alkoxycarbonyl; or
  $R^3$ and $R^4$ together with N is pyrrolidino, piperidino, morpholino, thiomorpholino or piperazino, wherein the piperazino is optionally substituted at the 4-position by —C(O)R⁸ where R⁸ is hydrogen, lower alkyl, lower alkoxy or amino;

or a pharmaceutically acceptable salt thereof; which process comprises the following steps:

(1) reacting the compound of formula (B):

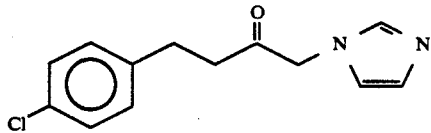
(B)

with a compound of formula (D):

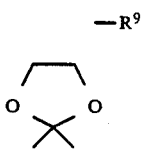
(D)

wherein R⁹ is halo, tosylate or mesylate, in the presence of a strong acid selected from the group consisting of alkanesulfonic acids, arenesulfonic acids and Lewis acids, to yield a mixture of stereoisomers represented by the following formula (E):

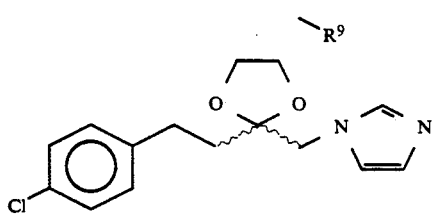
(E)

wherein R⁹ is halo, tosylate or mesylate;

(2) dissolving the mixture of stereoisomers represented by formula (E), as defined above, in a suitable solvent and treating the resulting solution with about 0.5 to about 2.0 molar equivalents of concentrated nitric acid to yield a compound of formula (Eb):

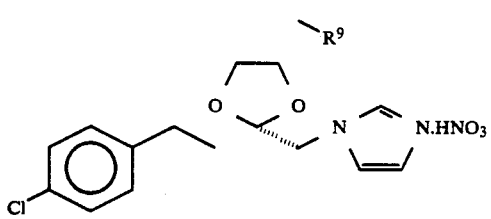
(Eb)

wherein R⁹ is halo, tosylate or mesylate, as a precipitate;

(3) treating the mother liquor resulting from the preparation of the compound of formula (Eb) with a suitable base and allowing the resulting mixture to crystallize from a suitable solvent to yield a compound of formula (Ea):

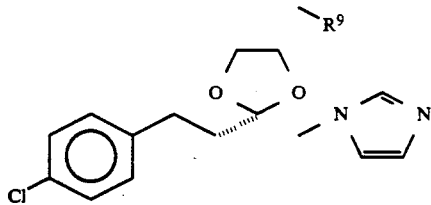
(Ea)

wherein R⁹ is halo, tosylate or mesylate; and (4) treating a compound of formula (Ea), as defined above, with a compound of formula (F):

(F)

wherein n is 0, 1 or 2;

each R¹ is independently halo or lower alkyl;

R² is nitro or —N(R³)R⁴ where

R³ is hydrogen or lower alkyl;

R⁴ is hydrogen, lower alkyl, lower alkylsulfonyl or —C(Y)R⁵ where Y is oxygen or sulfur and R⁵ is hydrogen, lower alkyl, lower alkoxy or —N(R⁶)R⁷ where R⁶ is hydrogen or lower alkyl and R⁷ is hydrogen, lower alkyl or lower alkoxycarbonyl; or R³ and R⁴ together with N is pyrrolidino, piperidino, morpholino, thiomorpholino or piperazino, wherein the piperazino is optionally substituted at the 4-position by —C(O)R⁸ where R⁸ is hydrogen, lower alkyl, lower alkoxy or amino;

in the presence of base to yield a compound of formula (I), as defined above.

In another aspect, the present invention provides for the recycling of the compounds of formula (Eb) so formed as starting materials for the mixture of stereoisomers represented by formula (E) as described above. This recycling comprises the following additional steps to the process described above:

(5) treating the compound of formula (Eb) so formed with a suitable base to yield a compound of formula (Ec):

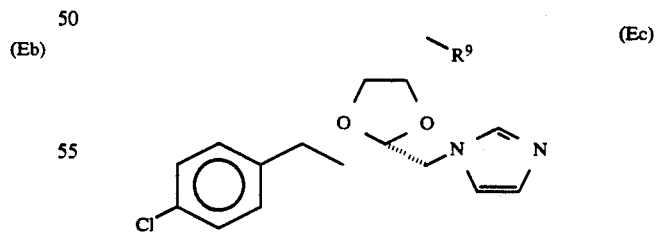
(Ec)

wherein R⁹ is halo, tosylate or mesylate; and (6) treating the compound of formula (Ec) so formed with a strong acid selected from the group consisting of alkanesulfonic acids, arenesulfonic acids and Lewis acids, to yield the mixture of stereoisomers represented by formula (E), as defined above in Step (1).

The mixture of stereoisomers as represented by formula (E) so formed by this recycling process can then be further treated as described above in Steps (2), (3)

and (4) of the process to produce the compounds of formula (I).

In another aspect, the present invention provides for the preparation of compounds of formula (B) for use in Step (1) of the process described herein. The preparation comprises treating the compound of formula (A):

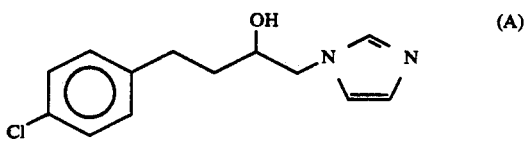

with dimethyl sulfoxide, which has been activated by an organic nitrogenous base-sulfur trioxide complex, in the presence of an organic base to yield the compound of formula (B).

In another aspect, the present invention provides for the separation of compounds of formula (Ea):

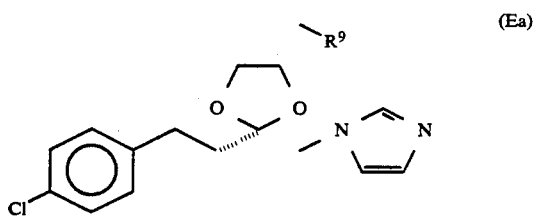

wherein $R^9$ is halo, tosylate or mesylate, from a mixture of stereoisomers represented by the following formula (E):

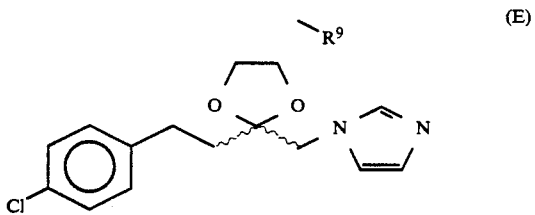

wherein $R^9$ is halo, tosylate or mesylate; which process comprises the following steps:

(a) dissolving the mixture of stereoisomers represented by formula (E), as defined above, in a suitable solvent and treating the resulting solution with about 0.5 to about 1.5 molar equivalents of concentrated nitric acid to yield a compound of formula (Eb):

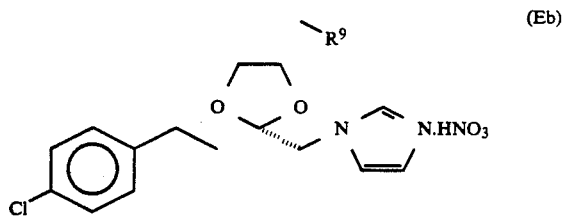

wherein $R^9$ is halo, tosylate or mesylate, as a precipitate; and (b) treating the mother liquor resulting from the preparation of the compound of formula (Eb) with a suitable base and then allowing the resulting mixture to crystallize from a suitable solvent to yield a compound of formula (Ea), as defined above.

DETAILED DESCRIPTION OF THE INVENTION

Definitions

As used in the specification and appended claims, unless specified to the contrary, the following terms have the meaning indicated:

The term "lower alkyl" refers to a straight or branched chain monovalent radical consisting solely of carbon and hydrogen, containing no unsaturation and having from one to four carbon atoms, e.g., methyl, ethyl, n-propyl, 1-methylethyl, n-butyl, 2,2-dimethylpropyl (tert-butyl), 1-methylpropyl, and the like.

The term "lower alkoxy" refers to a radical of the formula —$OR_a$ where $R_a$ is lower alkyl as defined above, e.g., methoxy, ethoxy, n-propoxy, 1-methylethoxy, n-butoxy, 2,2-dimethylpropoxy (tert-butoxy), and the like.

The term "halo" refers to a halogen radical, e.g., fluoro, chloro, bromo or iodo.

The term "amino" refers to the radical —$NH_2$.

The term "lower alkanesulfonyl" refers to a radical of the formula —$S(O)_2R_a$ where $R_a$ is lower alkyl as defined above, e.g., mesyl (methanesulfonyl), ethanesulfonyl, n-propanesulfonyl, n-butanesulfonyl, iso-butanesulfonyl, and the like.

The term "lower alkoxycarbonyl" refers to the radical of the formula —$C(O)R_b$ where $R_b$ is lower alkoxy as defined above, e.g., methoxycarbonyl, ethoxycarbonyl, n-propoxycarbonyl, n-butoxycarbonyl, 2-methylpropoxycarbonyl, and the like.

The term "aryl" refers to a phenyl or naphthyl radical optionally substituted by lower alkyl, e.g., 4-methylphenyl (p-tolyl), 3-methylphenyl (m-tolyl), and the like.

The term "optionally" means that the subsequently described event or circumstance may or may not occur, and that the description includes instances where the event or circumstance occurs and instances wherein it does not.

The term "alkanesulfonic acid" refers to an acid of the formula $R_aS(O)_2OH$ where $R_a$ is lower alkyl as defined above, e.g., methanesulfonic acid, ethanesulfonic acid, and the like. This term includes those alkanesulfonic acids which are covalently bonded to an inert polymer for stability and ease of handling.

The term "arenesulfonic acid" refers to an acid of the formula $R_cS(O)_2OH$ where $R_c$ is aryl as defined above, e.g., p-toluenesulfonic acid, 1-naphthalenesulfonic acid, 2-naphthalenesulfonic acid, and the like. This term includes those arenesulfonic acids which are covalently bonded to an inert polymer for stability and ease of handling.

The term "tosylate" refers to a radical of the formula —$OS(O)_2R_d$ where $R_d$ is 4-methylphenyl (p-tolyl).

The term "mesylate" refers to a radical of the formula —$OS(O)_2CH_3$.

The term "organic nitrogenous base-sulfur trioxide complex" refers to a complex of the formula $R_e\cdot SO_3$ where $R_e$ is an organic nitrogenous base selected from the group consisting of tertiary amines, e.g., triethylamine, trimethylamine, diisopropylethylamine, and the like; and cyclic amines, e.g., pyridine, pyrrolidine, morpholine, N-methylmorpholine, N-methylpyridine and the like. This term includes those organic nitrogenous base-sulfur trioxide complexes which are covalently bonded to an inert polymer for stability and ease of handling.

The term "mother liquor" refers to the residual solution which remains after the precipitation of a compound of formula (Eb) in Step (2) of the process described herein.

The term "concentrated nitric acid" refers to 68% to 72% aqueous nitric acid.

The term "stereoisomers" refers to compounds having identical molecular formulae and nature or sequence of bonding but differing in the arrangement of their atoms in space.

For purposes of Steps (1) and (6) of the process disclosed herein, the term "strong acid" refers to alkanesulfonic acids, as defined above, e.g., methanesulfonic acid; arenesulfonic acids, as defined above, e.g., p-toluenesulfonic acid; and Lewis acids, e.g., titanium tetrachloride and aluminum chloride. The term also refers to those alkysulfonic acids, arenesulfonic acids and Lewis acids which are covalently bond to an inert polymer for stability and ease of handling.

For purposes of Step (2) of the process disclosed herein wherein the mixture of stereoisomers represented by formula (E) is dissolved in a suitable solvent, the term "suitable solvent" refers to those solvents which are capable of dissolving the mixture of stereoisomers represented by formula (E) and which allow for the precipitation of the corresponding compound of formula (Eb).

For purposes of Step (3) of the process disclosed herein wherein the mother liquor resulting from the preparation of the compound of formula (Eb) is treated with a suitable base, the term "suitable base" refers to those bases capable of raising the pH of the mother liquor to a pH of between about 10-11, preferably to a pH of about 10. Exemplary of such suitable bases include, but are not limited to, sodium hydroxide and triethylamine.

For purposes of Step (3) of the process disclosed herein wherein the resulting mixture from the basification of the mother liquor is allowed to crystallize from a suitable solvent, the term "suitable solvent" refers to those solvents which are capable of dissolving the resulting mixture and which allow for the crystallization of the compound of formula (Ea). Exemplary of such solvents are ketones, e.g., acetone; alcohols, e.g., isopropanol; ethers, e.g., diethyl ether; and esters, e.g., ethyl acetate; and combinations of two or more of such solvents. The preferred suitable solvent for the crystallization is isopropanol.

For purposes of Step (4) of the process wherein a compound of formula (Ea) is treated with a compound of formula (F) to yield a compound of formula (I), the term "base" refers to an inorganic base strong enough to allow for the formation of the anion of the compound of formula (F) during the reaction disclosed therein. Exemplary of such a base is potassium carbonate.

For purposes of Step (5) of the process wherein a compound of formula (Eb) is treated with a suitable base to form a compound of formula (Ec), the term "suitable base" refers to those bases capable of raising the pH of the solution containing the compound of formula (Eb) to a pH of between 9-11, preferably to a pH of about 10. Exemplary of such bases include, but are not limited to, sodium hydroxide and N-methylmorpholine.

The term "inert solvent" refers to a solvent inert under the conditions of the reaction being described in conjunction therewith, e.g., benzene, toluene, methylene chloride, acetonitrile, hexane, tetrahydrofuran ("THF"), xylene, and the like.

For purposes of the oxidation of the compound of formula (A) to yield a compound of formula (B), the term "organic base" refers to tertiary amines, e.g., trimethylamine, triethylamine, diisopropylethylamine, N-methylmorpholine, and the like.

For clarification purposes, Steps (a) and (b) of the process for separating a compound of formula (Ea) from a mixture of stereoisomers represented by formula (E), as set forth above in the Summary of the Invention, are essentially the same reaction steps as Steps (2) and (3) of the process for preparing compounds of formula (I), as set forth above in the Summary of the Invention.

For purposes of converting the compounds of formula (I) into corresponding pharmaceutically acceptable salts, the term "acid" refers to those acids capable of forming stable pharmaceutically acceptable salts of the compounds of formula (I), e.g., hydrochloric acid, oxalic acid, nitric acid, sulfuric acid, maleic acid, methanesulfonic acid, and the like; preferably hydrochloric acid.

"Pharmaceutically acceptable salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

It is understood, for purposes of this invention, that the compounds of formula (I) do not include those compounds wherein n is 2 and the two $R^1$ substituents are adjacent tert-butyl groups.

The yield of each of the reactions described herein is expressed as a percentage of the theoretical yield.

The nomenclature used herein is basically a modified form of I.U.P.A.C. nomenclature wherein compounds of formula (I), and intermediates thereof, are named as derivatives of 1,3-dioxolane. The following numbering system will be used for naming the compounds:

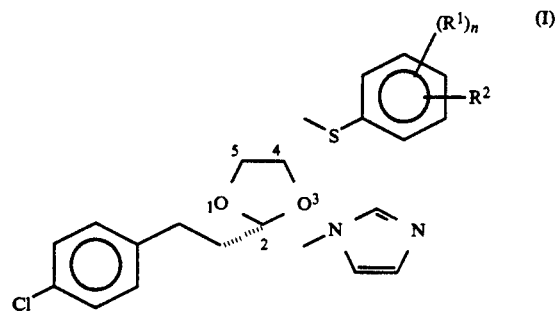

The compounds of formula (I), their pharmaceutically acceptable salts, and intermediates thereof, have at least two asymmetric carbon atoms in their structure, namely the 2-carbon and 4-carbon of the dioxolane ring, and therefore can exist as distinct stereoisomers. All such stereoisomers, and their pharmaceutically acceptable salts, are intended to be within the scope of this invention.

Compounds of formula (I) have the substituent at the 2-position of the dioxolane ring and the substituent at the 4-position of the dioxolane ring on the same side of the plane of the dioxolane ring, and are designated herein as the cis-stereoisomers. The corresponding trans-stereoisomers are those compounds which have the substituent at the 2-position of the dioxolane ring and the substituent at the 4-position of the dioxolane ring on opposite sides of the plane of the dioxolane ring.

An absolute descriptor, R or S, may be assigned to the chiral carbon atoms in the individual stereoisomers according to the "Sequence Rule" procedure of Cahn, Ingold and Prelog.

For example, a compound of formula (I) wherein n is 0 and $R^2$ is —$NH_2$, i.e., the compound of the following formula:

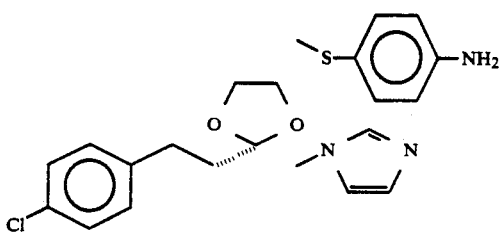

is named herein as (2S,4S)-cis-2-(2-(4-chlorophenyl)ethyl)-2-(imidazol-1-yl)methyl-4-(4-aminophenylthio)-methyl-1,3-dioxolane.

PREFERRED EMBODIMENTS

Among the compounds of formula (I) and their pharmaceutically acceptable salts, as described above in the Summary of the Invention, a preferred group of compounds prepared by the process disclosed herein are those compounds of formula (I) wherein n is 0.

A preferred subgroup of these compounds are those compounds of formula (I) wherein $R^2$ is in the 4-position and is —$N(R^3)R^4$ where $R^3$ is hydrogen or lower alkyl and $R^4$ is hydrogen, lower alkyl, lower alkylsulfonyl or —$C(Y)R^5$ where Y is oxygen or sulfur and $R^5$ is hydrogen, lower alkyl, lower alkoxy or —$N(R^6)R^7$ where $R^6$ is hydrogen or lower alkyl and $R^7$ is hydrogen, lower alkyl or lower alkoxycarbonyl.

A preferred class of these compounds are those compounds of formula (I) wherein $R^3$ is hydrogen and $R^4$ is hydrogen or —$C(Y)R^5$ where Y is oxygen and $R^5$ is hydrogen, lower alkyl or lower alkoxy.

A preferred subclass of these compounds are those compounds of formula (I) wherein $R^4$ is hydrogen or acetyl.

Presently, the most preferred compounds of formula (I) prepared by the process disclosed herein are the following: (2S,4S)-cis-2-(2-(4-chlorophenyl)ethyl)-2-(imidazol-1-yl)methyl-4-(4-aminophenylthio) methyl-1,3-dioxolane; and (2S,4S)-cis-2-(2-(4-chlorophenyl)ethyl)-2-(imidazol-1-yl)methyl-4-(4-acetamidophenylthio)methyl-1,3-dioxolane. Particularly preferred are the pharmaceutically acceptable salts of these compounds, particularly those formed with hydrochloric acid.

Within the process described herein, several reagents and conditions are preferred. For example, in Step (1) of the process, it is preferred to use compounds of formula (D) where $R^9$ is tosylate. In addition, in Step (1) it is preferred that the strong acid is selected from the group consisting of methanesulfonic acid and p-toluenesulfonic acid. It is particularly preferred to use methanesulfonic acid in Step (1).

It is also preferred that in Step (2) of the process the amount of concentrated nitric acid used to treat compounds of formula (E) is between about 0.8 and about 1.0 molar equivalents.

It is also preferred to recycle the compounds of formula (Eb) so formed in the process by treating such compounds with a suitable base to yield the corresponding free bases, i.e., the compounds of formula (Ec), and to further treat these compounds of formula (Ec) so formed with methanesulfonic acid to yield a mixture of stereoisomers as represented by formula (E), which can then be further treated as in Step (2) of the process described above in order to separate out the compounds of formula (Ea) from the mixture of stereoisomers represented by formula (E).

It is also preferred to prepare the compound of formula (B) used in the process described herein by treating a compound of formula (A) with dimethyl sulfoxide, which has been activated by a trimethylamine-sulfur trioxide complex, in the presence of an organic base, preferably triethylamine.

Presently, the preferred process of the invention involves the preparation of compounds of formula (I):

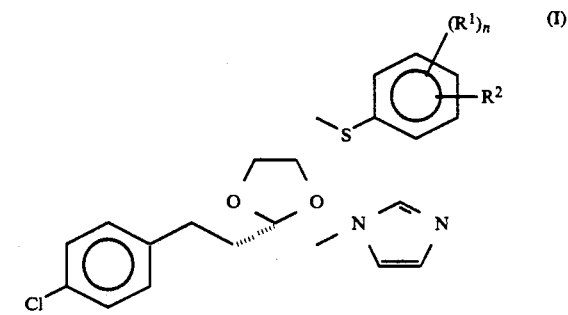

wherein:
n is 0;
$R^2$ is —$N(R^3)R^4$ where $R^3$ is hydrogen and $R^4$ is hydrogen or —$C(Y)R^5$ where Y is oxygen and $R^5$ is methyl, or a pharmaceutically acceptable salt thereof;
which preparation comprises the following steps:
(1) reacting the compound of formula (B):

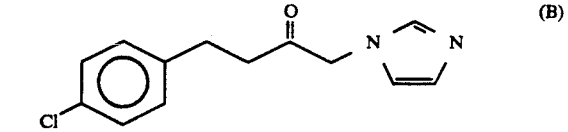

with a compound of formula (D):

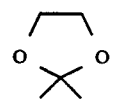

wherein $R^9$ is tosylate, in the presence of methanesulfonic acid, to yield a mixture of stereoisomers represented by the following formula (E):

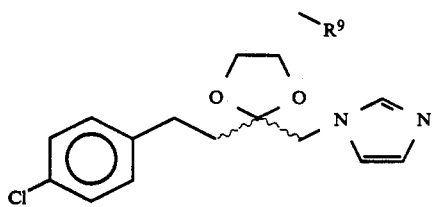

(E)

wherein R$^9$ is tosylate;

(2) dissolving the mixture of stereoisomers represented by formula (E), as defined above, in a suitable solvent and treating the resulting solution with about 0.8 to about 1.0 molar equivalents of concentrated nitric acid to
yield a compound of formula (Eb):

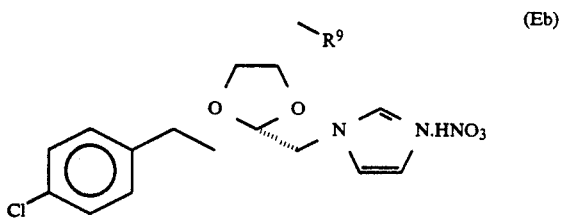

(Eb)

wherein R$^9$ is tosylate, as a precipitate;

(3) treating the mother liquor resulting from the preparation of the compound of formula (Eb) with sodium hydroxide and then allowing the resulting mixture to crystallize from isopropanol to yield a compound of formula (Ea):

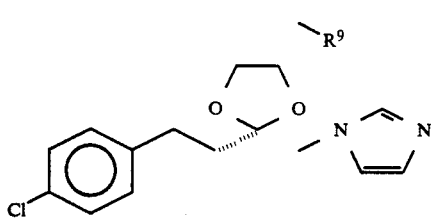

(Ea)

wherein R$^9$ is tosylate;

(4) treating a compound of formula (Ea), as defined above, with a compound of formula (F):

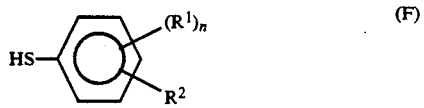

(F)

wherein
n is 0; and
R$^2$ is —N(R$^3$)R$^4$ where R$^3$ is hydrogen and R$^4$ is hydrogen or —C(Y)R$^5$ where Y is oxygen and R$^5$ is methyl;
in the presence of potassium carbonate to yield a compound of formula (I), as defined above.

It is more preferred that the compound prepared by this process is (2S,4S)-cis-2-(2-(4-chlorophenyl)ethyl)-2-(imidazol-1-yl)-methyl-4-(4-aminophenylthio)methyl-1,3-dioxolane, or the corresponding dihydrochloride salt thereof.

It is also more preferred to recycle the compound of formula (Eb) formed in this process back into the process by treating such compound with sodium hydroxide to yield a compound of formula (Ec); which can then be treated with methanesulfonic acid to yield the mixture of stereoisomers represented by formula (E).

It is also more preferred that the compound of formula (B) used in this process is prepared by treating a compound of formula (A) with dimethyl sulfoxide, which has been activated by a trimethylamine-sulfur trioxide complex, in the presence of triethylamine, to yield a compound of formula (B).

Preparation of Compounds of Formula (I)

A. Preparation of Starting Materials

The compound of formula (B) is a starting material in the preparation of compounds of formula (I). It can be prepared by methods disclosed in co-pending U.S. patent application Ser. No. 07/633,599, or by methods known to one of ordinary skill in the art, for example, by the method of Swern using dimethyl sulfoxide activated by, e.g., oxalyl chloride (see, e.g., *J. Org. Chem.* (1979), Vol. 44, NO. 23, p. 4148. Alternatively, the compound of formula (B) can be prepared as shown in the following Reaction Scheme 1:

REACTION SCHEME 1

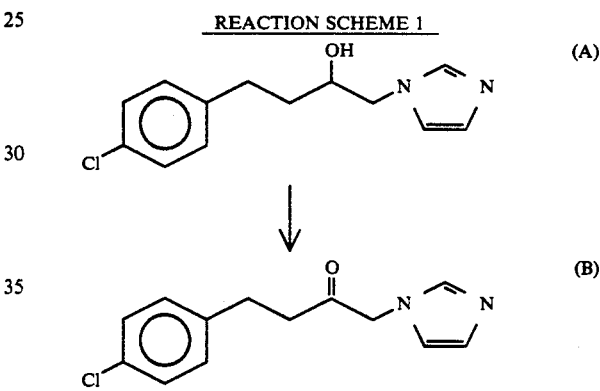

In general, a compound of formula (B) may be prepared by this Reaction Scheme by treating a compound of formula (A) with dimethyl sulfoxide (DMSO), which has been activated by an organic nitrogenous base-sulfur trioxide complex, in the presence of an organic base. The starting compound of formula (A) may be prepared according to the methods described in U.S. Pat. Nos. 4,518,607 and 4,078,071 (Syntex); or by the methods described in *J. Med. Chem.* (1978), Vol. 21, p. 840, and *J. Amer. Chem. Soc.* (1930), Vol. 52, p. 1164; or by the method described in co-pending U.S. patent application Ser. No. 07/633,599. The organic nitrogenous base-sulfur trioxide complexes are commercially available, for example, from Aldrich Company, or can be prepared by methods known to those of ordinary skill in the art (see, e.g., "The Reactions of Sulfur Trioxide, and of Its Adducts, with Organic Compounds," *Chem. Rev.* (1962), Vol. 62, pp. 550–555).

In particular, the compound of formula (A) is treated with an excess of DMSO, which has been activated with about 2 to 5 molar equivalents, preferably abut 2.25 molar equivalents, of an organic nitrogenous base-sulfur trioxide complex, e.g., trimethylamine-sulfur trioxide complex or pyridine-sulfur trioxide complex, preferably trimethylaminesulfur trioxide complex. This reaction is carried out in the presence of an excess amount of an organic base, e.g., preferably triethylamine, and in an inert solvent, preferably methylene chloride, at a temperature of about 20°–40° C., preferably at about 36°–38° C., for about 10–24 hours, preferably for about 16 hours. The compound of formula (B) is then isolated from the reaction mixture by conventional means, preferably by extraction or filtration.

Compounds of formula (D), i.e., 3-chloro-1,2-propanediol acetonide, S-solketal tosylate and S-solketal mesylate, are also starting materials in the preparation of compounds of formula (I). One compound of formula (D), i.e., S-solketal tosylate, is commercially available, e.g., from Fluka, International Bio-Synthetics (IBIS) or Chemi S.p.A. The compounds of formula (D) can also be prepared by methods known to those of ordinary skill in the art. For example, the tosylate and the mesylate can be prepared by treating the corresponding R-solketal with tosyl or mesyl chloride in the presence of excess organic base, such as pyridine, to yield the corresponding S-solketal tosylate and S-solketal mesylate. 3-chloro-1,2-propanediol acetonide may be prepared from S-3-chloro-1,2-propanediol by standard ketalization methods known to those of ordinary skill in the art, e.g., acid catalyzed ketalization or transketalization reaction.

B. Preparation of Intermediates

Compounds of formulae (Ea) and (Eb) are intermediates in the preparation of compounds of formula (I) and are prepared as shown in the following Reaction Scheme 2 wherein $R^9$ is halo, tosylate or mesylate:

REACTION SCHEME 2

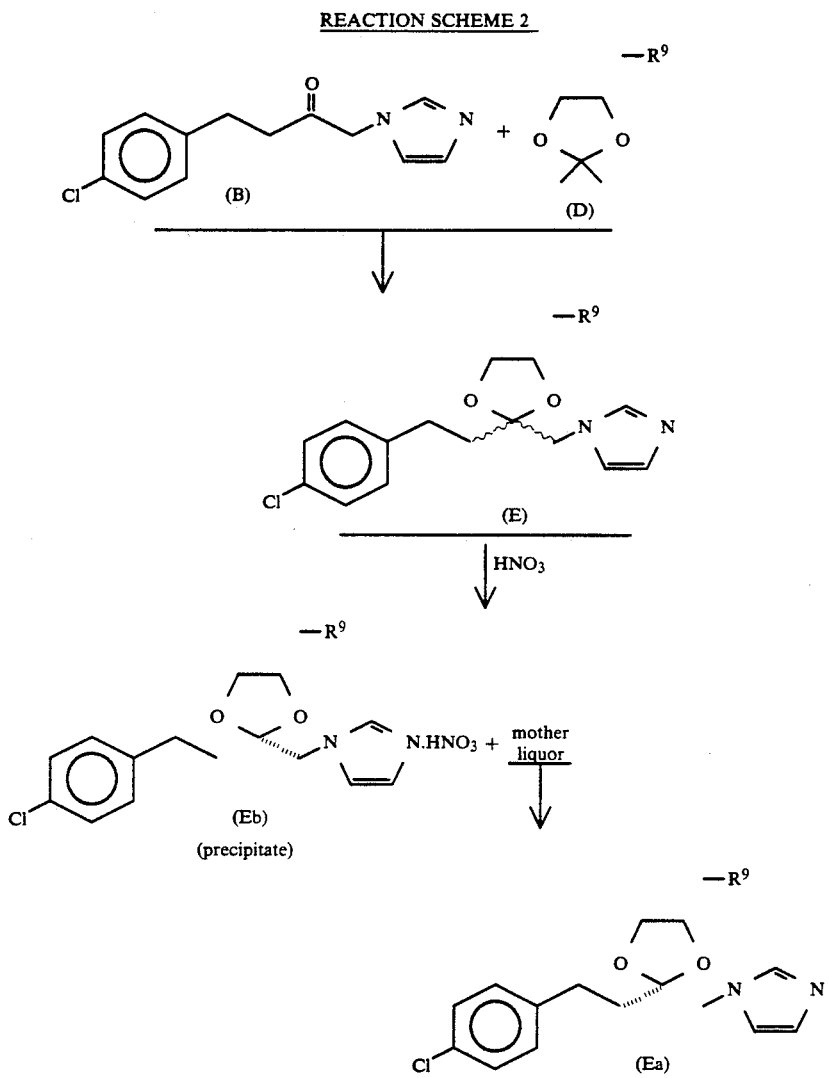

In general, compounds of formulae (Ea) and (Eb) are prepared by first treating the compound of formula (B) with a compound of formula (D) wherein $R^9$ is halo, tosylate or mesylate, in the presence of a strong acid, to yield the mixture of stereoisomers represented by formula (E) wherein $R^9$ is halo, tosylate or mesylate. The compound of formula (E) is then treated with concentrated nitric acid to yield a compound of formula (Eb) as a precipitate. The resulting mother liquor is then treated with a suitable base and the resulting mixture is then allowed to crystallize from a suitable solvent to yield a compound of formula (Ea).

In particular, the compound of formula (B) is treated with excess molar equivalants, preferably about 1.25 molar equivalents, of a compound of formula (D) wherein $R^9$ is halo, tosylate or mesylate, in the presence of a strong acid, e.g., an alkanesulfonic acid, an arenesulfonic acid or a Lewis acid, preferably methanesulfonic acid, in a suitable solvent, preferably methylene chloride, while maintaining the temperature of the reaction mixture at about 15°-30° C., preferably room temperature. The reaction mixture is heated to about 30°-40° C. and stirred at that temperature for about 2-6 hours, preferably for about 3 hours. The reaction mixture is then allowed to cool to room temperature and concentrated. The residue is then dissolved in a suitable solvent, preferably ethyl acetate. The resulting solution is then made basic (pH 9-11) by a suitable base, preferably sodium hydroxide to form the free base, i.e., a compound of formula (E). The compound of formula (E) so formed is then treated with about 0.5 to about 2.0 molar equivalents of concentrated nitric acid, preferably 0.8 to about 1.0 molar equivalents of concentrated nitric acid. The resulting slurry is then allowed to stand at 20°-40° C., preferably at 27°-30° C., for about 1 to 4 hours, preferably for about 1 to 2 hours. The corresponding compound of formula (Eb), which is the nitrate salt of the undesired trans-stereoisomer, is isolated by filtration as a precipitate. The mother liquor from the filtration is then made basic (pH of between 8-11, preferably between 9-11) by the addition of a suitable base, preferably sodium hydroxide. The solvent is removed by conventional methods, preferably by distillation, and the resulting residue is dissolved in a suitable solvent, preferably isopropanol, and then the corresponding compound of formula (Ea), which is the desired cis-stereoisomer, is isolated from the solution by crystallization at room temperature, preferably at 19°-21° C., for about 1 to 4 hours, preferably for about 1 to 2 hours.

Alternatively, a solution of a compound of formula (B) in an inert solvent, preferably methylene chloride, is concentrated by conventional methods, preferably by distillation (azeotropic drying). The resulting mixture is then treated with a strong acid, preferably methanesulfonic acid, and 1.0 to 2.0 molar equivalents, preferably 1.25 molar equivalents, of a compound of formula (D). The resulting mixture is stirred at 30°-50° C., preferably at 35°-40° C., for about 2 to 4 hours, preferably for about 3 hours, and then allowed to cool to room temperature. Water and an inert solvent, preferably hexane, is then added to the mixture and the resulting solution is made basic (pH of between 9 and 13, preferably between 12-13) by the addition of a suitable base, preferably sodium hydroxide. The corresponding compound of formula (E) is then isolated from the mixture by conventional methods, preferably by concentration of the solution and crystallization from an inert solvent, preferably hexane. The compound of formula (E) is then dissolved in a suitable solvent, preferably ethanol, and then treated with a 0.5 to 2.0 molar equivalents of concentrated nitric acid, preferably 0.8 to 1.0 molar equivalents of concentrated nitric acid, at 35°-45° C., preferably at 40°-43° C., for about 0.5 to 3 hours, preferably for about 0.5 to 1.5 hours. The corresponding compound of formula (Eb) precipitates out and the mother liquor from the precipitation is made basic by the addition of a suitable base, preferably sodium hydroxide. The solvent is removed by conventional methods, preferably by vacuum distillation. The resulting residue is dissolved in a water-immiscible solvent, such as methylene chloride, and the resulting solution concentrated. The corresponding compound of formula (Ea) is then crystallized from a suitable solvent, preferably isopropanol.

C: Reequilibration of Compounds of Formula (Eb)

Compounds of formula (Eb) can be recycled back into the reaction illustrated in Reaction Scheme 2 above by reequilibrating the compounds of formula (Eb) so formed to the mixture of compounds represented by formula (E) as shown in the following Reaction Scheme 3 where $R^9$ is halo, tosylate or mesylate:

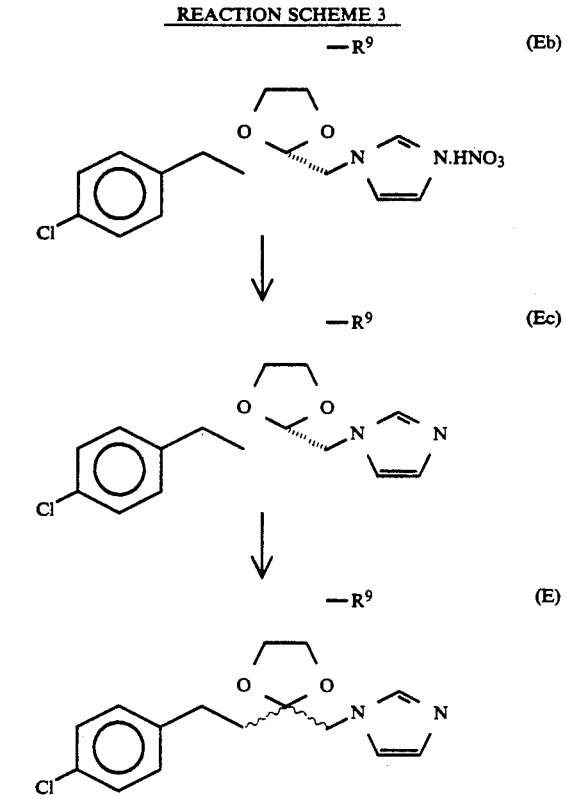

REACTION SCHEME 3

In general, compounds of formula (Eb), which are the nitrate salts of the undesired trans-stereoisomers formed in process illustrated in Reaction Scheme 2, are treated with a suitable base to yield the compounds of formula (Ec), which are the undesired trans-stereoisomers in their free base form. Compounds of formula (Ec) are then treated with a strong acid to form the mixture of cis-stereoisomers and trans-stereoisomers represented by formula (E). This mixture can then be introduced into the reaction illustrated in Reaction Scheme 2 and treated in the same manner as described therein to produce the separate stereoisomers, i.e., compounds of formulae (Ea) and (Eb). For example, the mixture can be treated with about 0.5 to about 1.5 molar equivalent amount, preferably with about 0.8 to about 1.0 molar equivalent amount of concentrated nitric acid, to form the compound of formula (Eb), which is the nitrate salt of the undesired trans-stereoisomer; and the resulting mother liquor can then be treated with a suitable base and the resulting mixture allowed to crystallize from a suitable solvent to yield a compound of formula (Ea).

In particular, a compound of formula (Eb) is dissolved in an inert solvent, preferably methylene chloride, and the resulting solution is then made basic (pH of between 9-11, preferably about 10) by the addition of a suitable base, preferably sodium hydroxide or N- methylmorpholine. The free base form of the compound of formula (Eb), i.e., the compound of formula (Ec), is then isolated by conventional methods, preferably by concentration. The compound of formula (Ec) is then treated with an excess molar equivalents, preferably 4 to 8 molar equivalents, of a strong acid selected from the group consisting of alkanesulfonic acids and Lewis acids, methanesulfonic acid, at 15°-30° C., preferably at 15°-25° C. The resulting solution is then heated at 37°-40° C. for about 1-6 hours, preferably for about 3-6 hours, and then allowed to cool to room temperature. The corresponding mixture of stereoisomers represented by formula (E) is then isolated from the solution by conventional methods, preferably by removal of the solvent through distillation. This mixture is then treated in a similar manner as described above in Section B to produce the separate stereoisomers, i.e. compounds of formulae (Ea) and (Eb).

Alternatively, the compound of formula (Ec) can be treated with an excess molar equivalents, preferably about 1.25 to 2.0 molar equivalents, of an arenesulfonic acid, such as p-toluenesulfonic acid, to form the mixture of stereoisomers represented by formula (E). This reaction is carried out at reflux temperatures in a high-boiling solvent, such as xylenes, and in the presence of a higher boiling alcohol, for example, n-butanol.

D. Preparation of compounds of formula (I)

Compounds of formula (I) are prepared from compounds of formulae (Ea) and (F) as shown in the following Reaction Scheme 4 wherein n, $R^1$, and $R^2$ are as defined above in the Summary of the Invention and $R^9$ is halo, tosylate or mesylate:

readily prepared according to methods known to one of ordinary skill in the art, e.g., according to the methods described in Coll. Czech. Chem. Commun. (1934), Vol. 6, No. 211; J. Amer. Chem. Soc. (1953), Vol. 75, p. 5281; Org. Prep. Procedures (1969), Vol. 1, pp. 87-90; or Chem. Listy (1952), vol. 46, pp. 237-40; or from the appropriate substituted phenol by the method described in J. Org. Chem. (1966), Vol. 31, p. 3980, by pyrolysis of the thionecarbamate and hydrolysis of the resulting thiolcarbamate.

In particular, compounds of formula (Ea) are treated with a 1 to 2 molar equivalent amount, preferably a 1.2 molar equivalent of a compound of formula (F) in the presence of a base, preferably anhydrous potassium carbonate, in an inert solvent, preferably acetone, and allowed to reflux for about 12-24 hours. The compound of formula (I) is then isolated from the reaction mixture by conventional methods, for example, distillation, extraction, and crystallization from a suitable solvent, preferably isopropanol.

In summary, compounds of formula (I) and their pharmaceutically acceptable salts are prepared by:

(1) reacting the compound of formula (B) with a compound of formula (D) wherein $R^9$ is halo, tosylate or mesylate, in the presence of a strong acid to yield a mixture of stereoisomers represented by the formula (E) wherein $R^9$ is halo, tosylate or mesylate;

(2) dissolving the mixture of stereoisomers represented by formula (E), as defined above, in a suitable solvent and treating the resulting solution with about 0.5 to about 2.0 molar equivalents of concentrated nitric acid to yield a compound of formula (Eb);

(3) treating the mother liquor resulting from the prep-

REACTION SCHEME 4

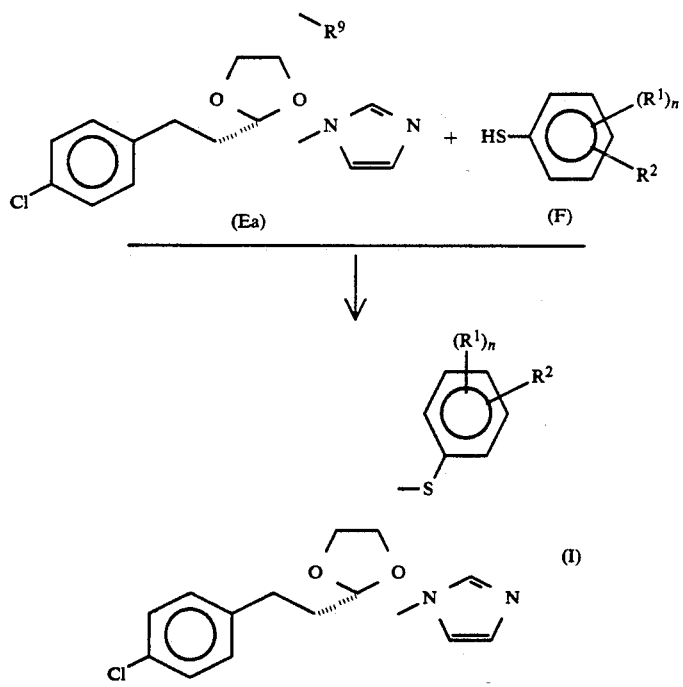

In general, compounds of formula (Ea) are treated with a compound of formula (F) in the presence of a base in an inert solvent to yield a compound of formula (I).

Compounds of formula (F) are commercially available, e.g., from Aldrich Chemical Co., or may be aration of the compound of formula (Eb) with a suitable base and allowing the resulting mixture to crystallize from a suitable solvent to yield a compound of formula (Ea) wherein $R^9$ is halo, tosylate or mesylate; and (4) treating a compound of formula (Ea) wherein $R^9$ is halo, tosylate or mesylate, with a compound of formula (F) wherein n is 0, 1 or 2; each $R^1$ is independently halo or lower alkyl; $R^2$ is nitro or $-N(R^3)R^4$ where $R^3$ is hydrogen or lower alkyl; $R^4$ is hydrogen, lower alkyl, lower alkylsulfonyl or $-C(Y)R^5$ where Y is oxygen or sulfur and $R^5$ is hydrogen, lower alkyl, lower alkoxy or $-N(R^6)R^7$ where $R^6$ is hydrogen or lower alkyl and $R^7$ is hydrogen, lower alkyl or lower alkoxycarbonyl; or $R^3$ and $R^4$ together with N is pyrrolidino, piperidino, morpholino, thiomorpholino or piperazino, wherein the piperazino is optionally substituted at the 4-position by $-C(O)R^8$ where $R^8$ is hydrogen, lower alkyl, lower alkoxy or amino, to form a compound of formula (I) as defined above in the Summary of the Invention.

Furthermore, the mixture of stereoisomers represented by formula (E) may be prepared by:

(5) treating the compound of formula (Eb) so formed in the above process with a suitable base to yield a compound of formula (Ec) wherein $R^9$ is halo, tosylate or mesylate;

(6) treating the compound of formula (Ec) so formed with a strong acid to yield the mixture of stereoisomers represented by formula (E).

In addition, all compounds of formula (I) that exist in the free base form may be converted to their pharmaceutically acceptable salts by treatment with the appropriate inorganic or organic acid. Salts of the compounds of formula (I) can also be converted to the free base form or to another salt.

The following specific examples are provided as a guide to assist in the practice of the invention, and are not intended as a limitation on the scope of the invention.

EXAMPLE 1

Preparation of Compounds of Formula (B) (Reaction Scheme 1)

A. To a mixture of 1-(4-(4-chlorophenyl)-2-hydroxybutyl)-imidazole (9.0 kg, 35.9 mol) and trimethylaminesulfur trioxide complex, 2.25 equivalents (11.25 kg, 80.9 mol), was added triethylamine (45 L, 32.7 kg, 323 mol), dimethyl sulfoxide (40.5 L, 44.5 kg, 570 mol), and methylene chloride (18 L). The resulting mixture was heated to 36°-38° C. and stirred for a minimum of 16 hours. Reaction completion was monitored by thin layer chromatography (10% methanol/methylene chloride + 2% NH$_4$OH). Upon completion of reaction, the reaction mixture was cooled to 20°-22° C. The temperature was maintained below 27° C. while 40.5 liters of water were added over a period of 15 to 30 minutes. Hexane (54 L) was then slowly added over a period of 15 to 30 minutes at 20°-25° C. Water (81 L) was then added to the mixture over a period of 30-60 minutes while the temperature was maintained at 20°-25° C. The resulting mixture was allowed to stand at 20°-22° C. for 1 to 2 hours. The mixture was filtered and the filter cake washed twice with water and then twice with hexane and dried under vacuum at 48°-51° C. to afford 4-(4-chlorophenyl)-1-(imidazol-1-yl)butan-2-one, 8.30 kg (93% yield).

B. Alternatively, a mixture of 1-(4-(4-chlorophenyl)-2-hydroxybutyl)imidazole (1.8 kg, 7.18 mol), 2.25 equivalents of pyridine-sulfur trioxide complex and methylene chloride (8.6 L) stirred in the presence of excess dimethyl sulfoxide (19 L) and triethylamine (9 L) at 20°-35° C. for 3 hours. Upon completion of reaction, the mixture was combined with water (76 L) and hexane (34.4 L). The product was isolated, washed with water and hexane and dried to yield 4-(4-chlorophenyl)-1-(imidazol-1-yl)butan-2-one, 1.48 kg (83% yield).

EXAMPLE 2

Preparation of Compounds of Formula (D)

A. To a solution of p-toluenesulfonyl chloride (17.16 kg, 90.1 mol) in pyridine (15 L, 14.7 kg, 185 mol) at 25° C. was added 12 kg of R-solketal (90.9 mol) over 2 to 3 hours with moderate (15°-25° C.) cooling such that the temperature of the reaction mixture rose to 33°-37° C. and maintained in this range. The reaction mixture was stirred for 3 hours at 33°-37° C. Reaction completion was monitored by TLC (1:1 ethyl acetate/hexane). Water (90 L) and ethyl acetate (198 L) was added and the reaction mixture was stirred for 15 minutes. The organic layer was washed with dilute hydrochloric acid and water and the solvent removed under reduced pressure. The residue was redissolved twice in 72 L of toluene and the solvent removed under reduced pressure to yield S-solketal tosylate, 25.3 kg (97% yield).

B. In a similar manner, but replacing p-toluenesulfonyl chloride with methanesulfonyl chloride, S-solketal mesylate is made.

EXAMPLE 3

Preparation of Compounds of Formulae (Ea) and (Eb) (Reaction Scheme 2)

A. To a solution of 4-(4-chlorophenyl)-1-(imidazol-1-yl)butan-2-one (16.0 kg, 64.3 mol) in methylene chloride (69.5 L) was added methanesulfonic acid (28 L, 41.4 kg, 431 mol) while the temperature of the reaction mixture was maintained at 18°-25° C. S-Solketal tosylate (23.0 kg, 80.4 mol) was added to the reaction mixture while the temperature of the reaction mixtures was maintained at 18°-25° C. The reaction mixture was heated to 35°-40° C. and stirred for 3 hours and then overnight at 20°-22° C. Reaction completion was monitored by TLC (7% CH$_3$OH/CH$_2$Cl$_2$ + 2% NH$_4$OH). The solvent was removed under reduced pressure and the residue cooled to 20°-22° C. The residue was then dissolved in ethyl acetate (300 L) and cooled to 10° C. The solution was then made basic (pH 10-11) by aqueous sodium hydroxide. The organic layer was washed with aqueous sodium chloride and dried over anhydrous sodium sulfate overnight. Concentrated nitric acid (70%, 3.661 L, 57.5 mol), was added to the solution and the resulting slurry was allowed to stand at 27°-30° C. for 1 to 2 hours. The solution was filtered and the filter cake washed twice with ethyl acetate (70 L) and dried at 40°-45° C. to yield (2R,4S)-trans-2-(2-(4-chlorophenyl)ethyl)-2-(imidazol-1-yl)methyl-4-(p-toluenesulfonyloxy)methyl-1,3-dioxolane nitrate salt (compound of formula (Eb)), 13.42 kg (38.6 yield). The mother liquors from the filtration were combined and made basic (pH 9-10) with aqueous sodium hydroxide (50%). The organic layer was washed with water and the solvent removed by distillation at atmospheric pressure while the ethyl acetate was replaced with isopropanol until the pot temperature reached 83° C. and the ethyl acetate content was in the range of 1.0% to 1.5% and the final volume was about 115 liters. The solution was allowed to cool for 30 minutes, and if crystallization had not commenced the solution would be seeded with the desired product. The solution was allowed to crystallize at 19°-21° C. for 1 to 2 hours, then filtered to give (2S,4S)-cis-2-(2-(4-chlorophenyl)ethyl)-2-(imidazol-1-yl)methyl-4-(p-toluenesulfonyloxy)methyl-1,3-dioxolane (compound of formula (Ea)), 9.26 kg (30.2% yield).

B. In a similar manner, but replacing 4-(4-chlorophenyl)-1-(imidazol-1-yl)butan-2-one with other appropriately substituted compounds of formula (B), the following compounds of formulae (Ea) and (Eb) are made:

(2R,4S)-trans-2-(2-(4-chlorophenyl)ethyl)-2-(imidazol-1-yl)methyl-4-(methanesulfonyloxy) methyl-1,3-dioxolane nitrate salt;

(2S,4S)-cis-2-(2-(4-chlorophenyl)ethyl)-2-(imidazol-1-yl)methyl-4-(methanesulfonyloxy) methyl-1,3-dioxolane;

(2R,4S)-trans-2-(2-(4-chlorophenyl)ethyl)-2-(imidazol-1-yl)methyl-4-chloromethyl-1,3-dioxolane nitrate salt; and (2S,4S)-cis-2-(2-(4-chlorophenyl)ethyl)-2-(imidazol-1-yl)methyl-4-chloromethyl-1,3-dioxolane.

C. Alternatively, a solution of 4-(4-chlorophenyl)-1-(imidazol-1-yl)butan-2-one (1.5 kg, 6.04 mol) and methylene chloride (35 L) was concentrated to about 5.0 L by distillation (azeotropic drying). The solution was treated with methanesulfonic acid (3.7 kg) and S-solketal tosylate (2.2 kg, 7.7 mol) at 35°–40° C. for 3 hours and then overnight at 20°–22° C. Upon completion of reaction, the product was mixed with methylene chloride and water and made basic (pH 12–13) with sodium hydroxide. The organic layer was washed with water, concentrated and the crude product crystallized from hexane. The slurry was aged for 1 hour at 19°–23° C. The product (a compound of formula (E)) was isolated, washed with hexane and dried. The product (2.6 kg) was dissolved in ethanol and treated with 0.35 L of 70% nitric acid at 40°–43° C. for 0.5–1.5 hours. (2R,4S)-trans-2-(2-(4-chlorophenyl)ethyl)-2-(imidazol-1-yl)methyl-4-(p-toluenesulfonyloxy)methyl-1,3-dioxolane nitrate salt was isolated, washed with ethanol and dried (39% yield). The mother liquors were combined, basified (pH 9–10) with aqueous sodium hydroxide, and ethanol was removed by distillation under reduced pressure. The product was extracted into methylene chloride and washed with water. The organic layer, which was dried over sodium sulfate, was concentrated and the product was crystallized from isopropanol; product seeds may be added if necessary. The slurry was aged for at least 1 hour at 19°–22° C. The product, (2S,4S)-cis-2-(2-(4-chlorophenyl)ethyl)-2-(imidazol-1-yl)methyl-4-(p-toluenesulfonyloxy)methyl-1,3-dioxolane (compound of formula (Ea)) was isolated, washed with isopropanol and dried (31% yield).

D. Alternatively, a mixture of 4-(4-chlorophenyl)-1-(imidazol-1-yl)butan-2-one (1.05 kg, 4.22 mol), p-toluenesulfonic acid monohydrate (0.9 kg) and toluene (14 L) was dried by azeotropic distillation and refluxed with S-solketal tosylate (1.5 kg, 5.24 mol) and n-butanol (0.8 L) in a suitable glass vessel. Upon completion of reaction, the mixture was concentrated, basified (pH 9) with triethylamine and mixed with ethyl acetate and water. The organic layer was washed with water, concentrated and the crude product crystallized by the addition of hexane (25 L) at 20°–25° C. The product was isolated, washed with hexane, and dissolved in ethanol (20 L), treated with excess concentrated nitric acid (0.29 L) and aged for 0.25–0.5 hour at 20°–22° C.

(2R,4S)-trans-2-(2-(4-chlorophenyl)ethyl)-2-(imidazol-1-yl)methyl-4-(p-toluenesulfonyloxy) methyl-1,3-dioxolane nitrate salt was isolated, washed with ethanol and hexane and dried (43% yield). The mother liquors were combined and basified (pH 9) with triethylamine and decolorized by treatment with charcoal. Ethanol was removed by distillation under reduced pressure and the product was mixed with ethyl acetate and water. The organic layer was washed with water, dried over sodium sulfate and concentrated and the product crystallized from isopropanol (5 L), with the aid of product seeds if necessary. The slurry was aged for at least 1 hour at 19°–22° C. The product, (2S,4S)-cis-2-(2-(4-chlorophenyl)ethyl)-2-(imidazol-1-yl)methyl-4-(p-toluenesulfonyloxy)methyl-1,3-dioxolane (compound of formula (Ea)) was isolated, washed with isopropanol and hexane and dried (24% yield).

EXAMPLE 4

Reequilibration of Compounds of Formula (Eb)
(Reaction Scheme 3)

A. A mixture of (2R,4S)-trans-2-(2-(4-chlorophenyl)ethyl)-2-(imidazol-1-yl)methyl-4-(p-toluenesulfonyloxy)methyl-1,3-dioxolane nitrate salt (13.99 kg, 25.9 mol), methylene chloride (119 L, 159 kg) and water (21.3 L) was made basic (pH 10) with sodium hydroxide (50%, 2.28 L). The organic layer was washed with water, dried over sodium sulfate, and concentrated to about 42.8 L by distillation to yield a solution of the corresponding free base, i.e., (2R,4S)-trans-2-(2-(4-chlorophenyl)-ethyl)-2-(imidazol-1-yl)methyl-4-(p-toluenesulfonyloxy)-methyl-1,3-dioxolane (compound of formula (Ec)). To this solution was added methanesulfonic acid (16.7 kg, 11.3 L, 173 mol) at 15°–25° C. The resulting solution was heated for 3 hours at 37°–40° C. under nitrogen and allowed to stir overnight at 20°–22° C. Reaction completion was monitored by TLC (7% CH$_3$OH in CH$_2$Cl$_2$+2% NH$_4$OH). The methylene chloride was removed by distillation to yield the corresponding mixture of stereoisomers, i.e., (2RS,4S)-2-(2-(4-chlorophenyl)-ethyl)-2-(imidazol-1-yl)methyl-4-(p-toluenesulfonyloxy)-methyl-1,3-dioxolane (compound of formula (E)). Ethyl acetate (120 L, 108 kg) was added to the residue and the resulting solution was cooled to 10° C. and made basic (pH 10) with aqueous sodium hydroxide. The organic layer was washed with aqueous sodium chloride and dried over anhydrous sodium sulfate. Concentrated nitric acid (70%, 1.490 L, 23.4 mol), was added to the solution and the resulting solution was allowed to stand at 27°–30° C. for 1 to 2 hours. The solution was filtered and the filter cake washed twice with ethyl acetate (28.5 L) and dried at 40°–45° C. to yield (2R,4S)-trans-2-(2-(4-chlorophenyl)-ethyl)-2-(imidazol-1-yl)methyl-4-(p-toluenesulfonyloxy)methyl-1,3-dioxolane nitrate salt (compound of formula (Eb)), 5.43 kg (39.0 yield). The mother liquors from the filtration were combined and made basic (pH 10) with aqueous sodium hydroxide (50%). The organic layer was washed with water and the solvent removed by distillation at atmospheric pressure while the ethyl acetate was replaced with isopropanol until the pot temperature reached 83° C. and the ethyl acetate content was in the range of 1.0% to 1.5% and the final volume was about 43.3 liters. The solution was allowed to cool for 30 minutes, and if crystallization had not commenced the solution would have been seeded with the desired product. The solution was allowed to crystallize at 19°–21° C. for 1 to 2 hours, then filtered to give (2S,4S)-cis-2-(2-(4-chlorophenyl)ethyl)-2-(imidazol-1-yl)methyl-4-(p-toluenesulfonyloxy)methyl- 1,3-dioxolane (compound of formula (Ea)), 4.58 kg (37.2% yield).

B. Alternatively, a solution of (2R,4S)-trans-2-(2-(4-chlorophenyl)ethyl)-2-(imidazol-1-yl)methyl-4-(p-toluenesulfonyloxy)-methyl-1,3-dioxolane nitrate salt (1.1 kg, 2.03 mol), methylene chloride (8 L) and water was made basic (pH 9-10) with N-methylmorpholine; the organic layer was washed with water and concentrated with the aid of toluene. The product was refluxed with S-solketal tosylate (0.05 kg, 0.17 mol), predried p-toluenesulfonic acid (0.7 kg,), xylene (5.5 L) and n-hexanol (0.35 L). Upon completion of reaction, the mixture was made basic with N-methylmorpholine and concentrated under reduced pressure; the product was extracted into methylene chloride and washed with water. The organic layer was dried over sodium sulfate, concentrated, and dissolved in ethanol and treated with excess 70% nitric acid (0.26 L). The product, (2R,4S)-trans-2-(2-(4-chlorophenyl)ethyl)-2-(imidazol-1-yl)methyl-4-(p-toluenesulfonyloxy)methyl-1,3-dioxolane nitrate salt, was isolated, washed with ethanol and hexane and dried (36% yield). The mother liquors were combined and basified (pH 10) with triethylamine; ethanol was removed by distillation under reduced pressure and the product was mixed with methylene chloride and water. The organic layer was washed with water, dried over sodium sulfate and concentrated. The product was crystallized from isopropanol. The slurry was aged for at least 1 hour at 19°-22° C. The product, (2S,4S)-cis-2-(2-(4-chlorophenyl)ethyl)-2-(imidazol-1-yl)methyl-4-(p-toluenesulfonyloxy)methyl-1,3-dioxolane, was isolated, washed with isopropanol and hexane and dried (13% yield).

C. Alternatively, a solution of (2R,4S)-trans-2-(2-(4-chlorophenyl)-ethyl)-2-(imidazol-1-yl)methyl -4-(p-toluenesulfonyloxy)methyl-1,3-dioxolane nitrate salt (0.58 g, 1.07 mmol) and methylene chloride (5 mL) was made basic (pH 10) with sodium hydroxide (10%, 2.5 mL). The organic layer was evaporated to dryness to yield a cream solid (0.51 g). The cream solid was dissolved in methylene chloride (5.0 mL) and titanium tetrachloride (0.12 mL, 1.1 mmol) was added and the resulting solution stirred at 40° C. for 6 hours. The solution was drowned into 2.0 mL of sodium hydroxide (10%) and water and filtered. The organic layer was washed with water, dried, concentrated and replaced with hexane. The resulting precipitate was filtered, washed with hexane and air-dried to yield 0.44 g of a cream product, i.e., the corresponding mixture of stereoisomers represented by formula (E), which was comprised of 50% of a compound of formula (Ea), i.e., (2S,4S)-cis-2-(2-(4-chlorophenyl)-ethyl)-2-(imidazol-1-yl)methyl-4-(p-tolunenesulfonyloxy)-methyl-1,3-dioxolane and 50% of a compound of formula (Eb). i.e.. (2R,4S)-trans-2-(2(4-chlorophenyl)-ethyl)-2-(imidazol-1-yl)methyl-4-(p-tolunenesulfonyloxy)-methyl-1,3-dioxolane.

EXAMPLE 5

(Reaction Scheme 4)

A. To a solution of (2S,4S)-cis-2-(2-(4-chlorophenyl)ethyl)-2-(imidazol-1-yl)methyl-4-(p-tolunenesulfonyloxy)methyl-1,3-dioxolane (12.7 kg, 26.6 mol) and anhydrous potassium carbonate (6.6 kg) in acetone (101 L) was added a solution of p-aminothiophenol (3.98 kg, 31.84 mol) in acetone (26 L). The resulting solution was refluxed for 12-24 hours. Reaction completion was monitored by TLC (7% methanol/methylene chloride, 2% NH$_4$OH). The reaction mixture was then allowed to cool to 30°-35 ° C. Water was added (98.5 L) and the acetone removed by distillation under reduced pressure. The remaining reaction mixture was allowed to cool to 20°-25° C. Methylene chloride (127 L) was added and the resulting solution stirred for 10-15 minutes. The organic layer was removed and washed with brine and dried over sodium sulfate. Basic alumina (3.4 kg) was added and the resulting slurry stirred for 1 hour. The alumina was removed by filtration. The methylene chloride in the filtrate was removed by distillation at atmospheric pressure while being replaced by isopropanol until the pot temperature reached 83° C. and the final volume was 76 liters. The solution was allowed to cool for 30 minutes, and if crystallization had not commenced the solution would have been seeded with the desired product. The solution was allowed to crystallize at 20°-22° C. overnight and filtered. The resulting filter cake was washed with isopropanol to give (2S,4S)-cis-2-(2-(4-chlorophenyl)ethyl)-2-(imidazol-1-yl)methyl-4-(4-amino-phenylthio)methyl-1,3-dioxolane, 10.32 kg (90.2% yield).

B. In a similar manner, but replacing p-aminothiophenol with other appropriately substituted compounds of formula (F), the following compounds of formula (I) are made:

(2S,4S)-cis-2-(2-(4-chlorophenyl)ethyl)-2-(imidazol-1-yl)methyl-4-(4-acetamidoaminophenylthio)methyl-1,3-dioxolane;

(2S,4S)-cis-2-(2-(4-chlorophenyl)ethyl)-2-(imidazol-1-yl)methyl-4-(3-aminophenylthio)methyl-1,3-dioxolane;

(2S,4S)-cis-2-(2-(4-chlorophenyl)ethyl)-2-(imidazol-1-yl)methyl-4-(4-amino-2-methylphenylthio)methyl-1,3-dioxolane;

(2S,4S)-cis-2-(2-(4-chlorophenyl)ethyl)-2-(imidazol-1-yl)methyl-4-(4-(4-acetylpiperazino)phenyl)thio)-methyl-1,3-dioxolane;

(2S,4S)-cis-2-(2-(4-chlorophenyl)ethyl)-2-(imidazol-1-yl)methyl-4-(2-pyrrolidinophenylthio)methyl-1,3-dioxolane;

(2S,4S)-cis-2-(2-(4-chlorophenyl)ethyl)-2-(imidazol-1-yl)methyl-4-(2-piperidinophenylthio)methyl-1,3-dioxolane;

(2S,4S)-cis-2-(2-(4-chlorophenyl)ethyl)-2-(imidazol-1-yl)methyl-4-(4-nitrophenylthio)methyl-1,3-dioxolane;

(2S,4S)-cis-2-(2-(4-chlorophenyl)ethyl)-2-(imidazol-1-yl)methyl-4-(4-propylaminocarbonylaminophenylthio)methyl-1,3-dioxolane;

(2S,4S)-cis-2-(2-(4-chlorophenyl)ethyl)-2-(imidazol-1-yl)methyl-4-(4-(4-formylpiperazino)phenylthio)-methyl-1,3-dioxolane; and (2S,4S)-cis-2-(2-(4-chlorophenyl)ethyl)-2-(imidazol-1-yl)methyl-4-(4-(4-propionylcarbonylpiperazino)-phenylthio)methyl-1,3-dioxolane.

EXAMPLE 6

Salts of Compounds of Formula (I)

A mixture of (2S,4S)-cis-2-(2-(4-chlorophenyl)ethyl)-2-(imidazol-1-yl)methyl-4-(4-amino-phenylthio)methyl-1,3-dioxolane (10.3 kg, 24.0 mol), concentrated aqueous hydrochloric acid (4.037 L, 49.0 mol), isopropanol (30.9 L) and water (1.33 L) was heated to 60°-70° C. in a suitable glass vessel. The resulting solution was clarified by filtration, cooled to 42°-44° C. and diluted by the addition of acetone (154.5 L). The slurry was cooled to 19°-23° C. and allowed to crystallize for at least 2 hours.

The slurry was filtered and the filter cake was washed twice with 1:1 acetone/ethyl acetate (41.2 L) and dried at 53°–58° C. under reduced pressure to yield the dihydrochloride salt of (2S,4S)-cis-2-(2-(4-chlorophenyl)ethyl)-2-(imidazol-1-yl)methyl-4-(4-aminophenylthio)-methyl-1,3-dioxolane, 11.25 kg (93.4% yield).

While the present invention has been described with reference to the specific embodiments thereof, it should be understood by those skilled in the art that various changes may be made and equivalents may be substituted without departing from the true spirit and scope of the invention. In addition, many modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A process for the preparation of compounds of formula (I):

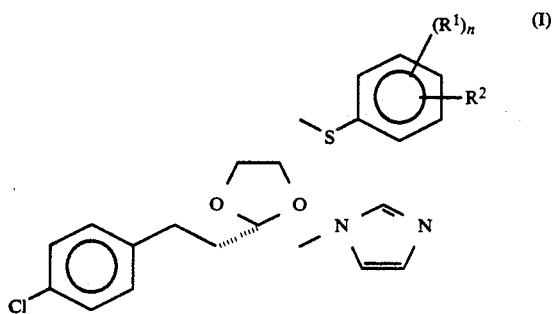

wherein:
n is 0;
$R^2$ is —$N(R^3)R^4$ where $R^3$ is hydrogen and $R^4$ is hydrogen or —$C(Y)R^5$ where Y is oxygen and $R^5$ is methyl, or a pharmaceutically acceptable salt thereof;
which process comprises the following steps:
(1) reacting the compound of formula (B):

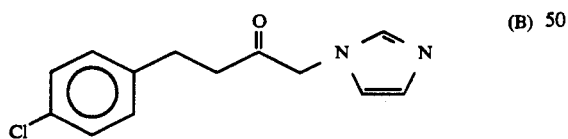

with a compound of formula (D):

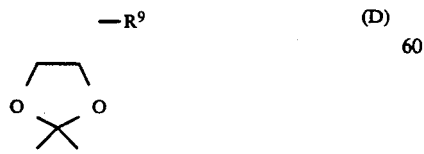

wherein $R^9$ is tosylate, in the presence of methanesulfonic acid, to yield a mixture of stereoisomers represented by the following formula (E):

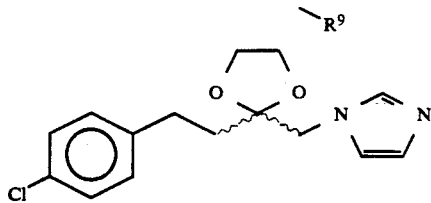

wherein $R^9$ is tosylate;

(2) dissolving the mixture of stereoisomers represented by formula (E), as defined above, in a suitable solvent and treating the resulting solution with about 0.8 to about 1.0 molar equivalents of concentrated nitric acid to yield a compound of formula (Eb):

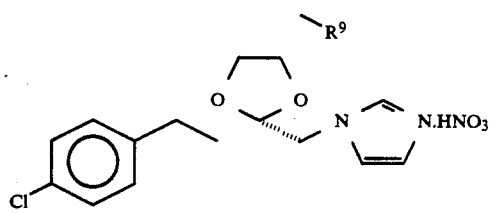

wherein $R^9$ is tosylate, as a precipitate;

(3) treating the mother liquor resulting from the preparation of the compound of formula (Eb) with sodium hydroxide and then allowing the resulting mixture to crystallize from isopropanol to yield a compound of formula (Ea):

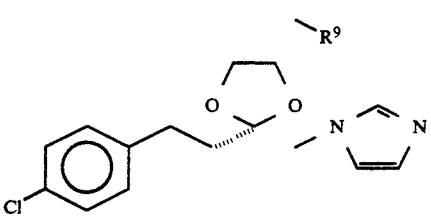

wherein $R^9$ is tosylate;

(4) treating a compound of formula (Ea), as defined above, with a compound of formula (F):

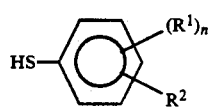

wherein
n is 0; and
$R^2$ is —$N(R^3)R^4$ where $R^4$ is hydrogen and $R^4$ is hydrogen or —$C(Y)R^5$ where Y is oxygen and $R^5$ is methyl; in the presence of potassium carbonate to yield a compound of formula (I), as defined above.

2. The process of claim 1 which further comprises converting the compound of formula (I) so formed into a pharmaceutically acceptable salt thereof by treating said compound with hydrochloric acid.

3. The process of claim 2 wherein the compound of formula (I) so formed is the dihydrochloride salt of (2S,4S)-cis-2-(2-(4-chlorophenyl)ethyl)-2-(imidazol-1-yl)-methyl-4-(4-aminophenylthio)methyl-1,3-dioxolane.

4. The process of claim 1 which further comprises the following steps:

(5) treating the compound of formula (Eb) so formed with sodium hydroxide to yield a compound of formula (Ec):

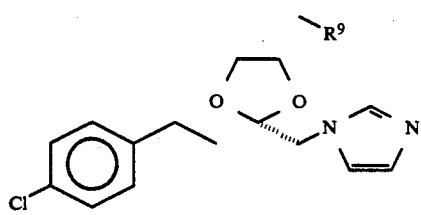

wherein R⁹ is tosylate;

(6) treating the compound of formula (Ec) so formed with methanesulfonic acid to yield the mixture of stereoisomers as represented by formula (E), as defined above in Step (1).

5. The process of claim 4 which further comprises converting the compound of formula (I) so formed into a pharmaceutically acceptable salt thereof by treating said compound with hydrochloric acid.

6. The process of claim 5 wherein the compound of formula (I) so formed is the dihydrochloride salt of (2S,4S)-cis-2-(2-(4-chlorophenyl)ethyl)-2-(imidazol-1-yl)-methyl-4-(4-aminophenylthio)methyl-1,3-dioxolane.

7. The process of claim 4 which further comprises the preparation of the compound of formula (B); which preparation comprises treating a compound of formula (A):

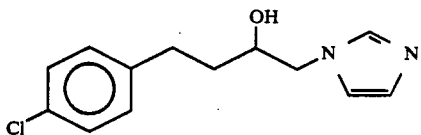

with dimethyl sulfoxide, which has been activated by a trimethylamine-sulfur trioxide complex, in the presence of triethylamine to yield the compound of formula (B), as defined above.

8. A process for separating a compound of formula (Ea):

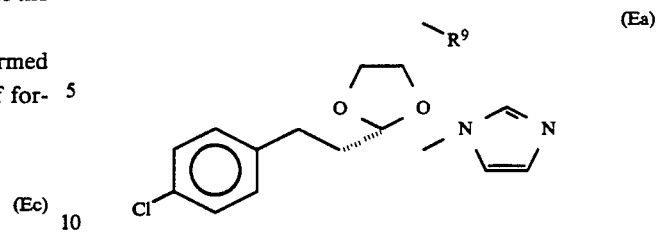

wherein R⁹ is halo, tosylate or mesylate, from a mixture of stereoisomers represented by the following formula (E):

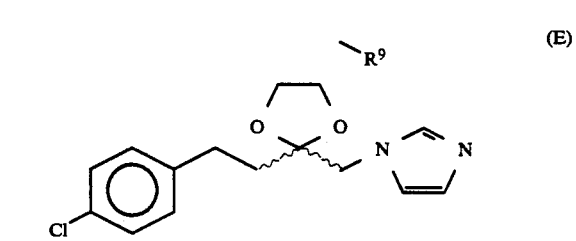

wherein R⁹ is halo, tosylate or mesylate; which process comprises the following steps:

(a) dissolving the mixture of stereoisomers represented by formula (E), as defined above, in a suitable solvent and treating the resulting solution with about 0.5 to about 1.5 molar equivalents of concentrated nitric acid to yield a compound of formula (Eb):

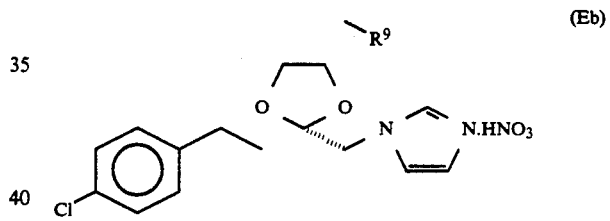

wherein R⁹ is halo, tosylate or mesylate, as a precipitate;

(b) treating the mother liquor resulting from the preparation of the compound of formula (Eb) with a suitable base and allowing the resulting mixture to crystallize from a suitable solvent to yield a compound of formula (Ea), as defined above.

9. The process of claim 8 where, in Step (a), the mixture of stereoisomers represented by formula (E) is treated with about 0.8 to about 1.0 molar equivalents of concentrated nitric acid.

10. The process of claim 8 wherein R⁹ is tosylate in the compound of formulae (E), (Ea) and (Eb).

UNITED STATES PATENT AND TRADEMARK OFFICE
CERTIFICATE OF CORRECTION

PATENT NO. : 5,274,108

DATED : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In the Abstract, formula (I) should appear as follows:

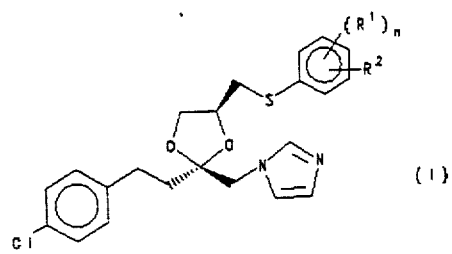

In column 1, lines 20-33, formula (I) should appear as follows:

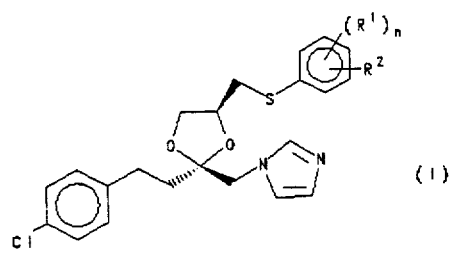

In column 2, lines 40-54, formula (I) should appear as follows:

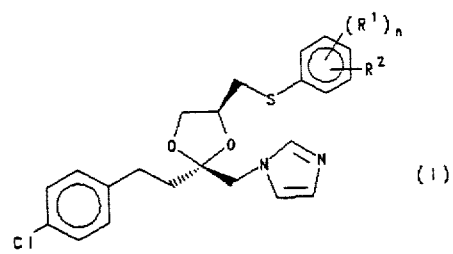

UNITED STATES PATENT AND TRADEMARK OFFICE
CERTIFICATE OF CORRECTION

PATENT NO. : 5,274,108

DATED : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In column 3, lines 16-24, formula (D) should appear as follows:

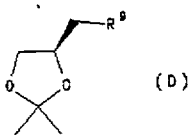

In column 3, lines 32-41, formula (E) should appear as follows:

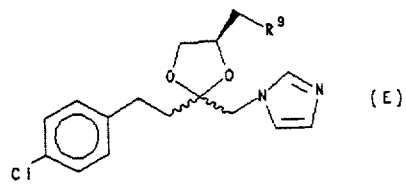

In column 3, lines 50-60 formula (Eb) should appear as follows:

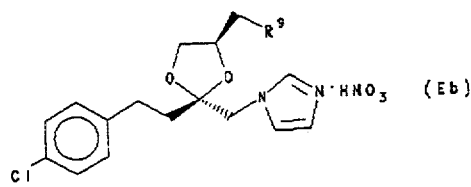

In column 4, lines 1-10 formula (Ea) should appear as follows:

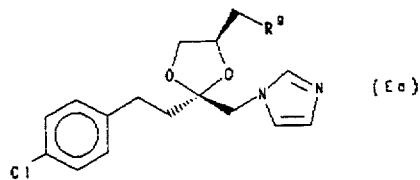

UNITED STATES PATENT AND TRADEMARK OFFICE
CERTIFICATE OF CORRECTION

PATENT NO. : 5,274,108

DATED : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In column 4, lines 50-58 formula (Ec) should appear as follows:

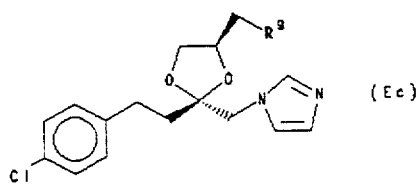

In column 5, lines 20-30 formula (Ea) should appear as follows:

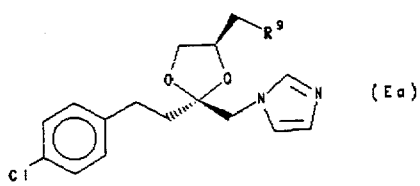

In column 5, lines 34-43, formula (E) should appear as follows:

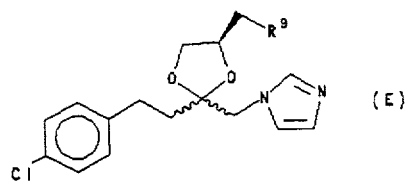

UNITED STATES PATENT AND TRADEMARK OFFICE
CERTIFICATE OF CORRECTION

PATENT NO. : 5,274,108
DATED : December 28, 1993
INVENTOR(S) : Norman H. Dyson, John O. Gardner, Anthony Prince, and Denis J. Kertesz It is certified that error appears in the above-identified patent and that said Letters Patent is hereby corrected as shown below:

In column 5, lines 52-60 formula (Eb) should appear as follows:

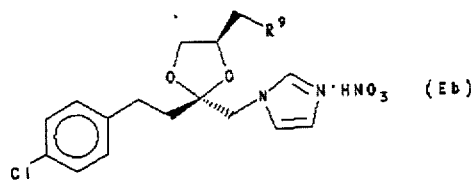

In column 8, lines 47-60, formula (I) should appear as follows:

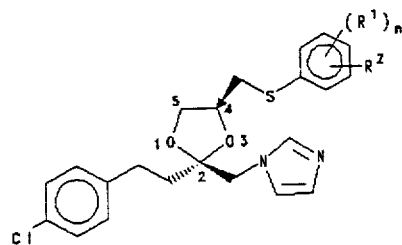

In column 9, lines 17-27, compound should appear as follows:

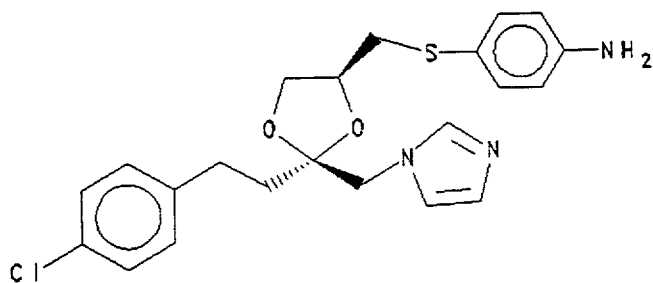

UNITED STATES PATENT AND TRADEMARK OFFICE
CERTIFICATE OF CORRECTION

PATENT NO. : 5,274,108

DATED : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In column 10, lines 27-41, formula (I) should appear as follows:

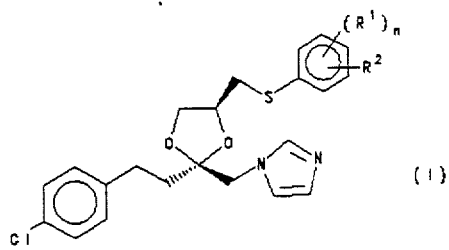

In column 10, lines 57-65, formula (D) should appear as follows:

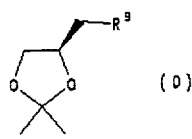

In column 11, lines 1-10, formula (E) should appear as follows:

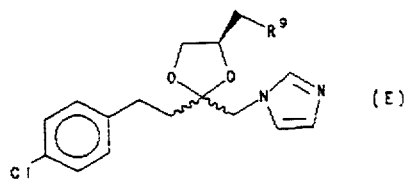

UNITED STATES PATENT AND TRADEMARK OFFICE
CERTIFICATE OF CORRECTION

PATENT NO. : 5,274,108

DATED : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In column 11, lines 18-28, formula (Eb) should appear as follows:

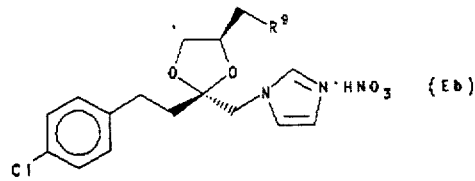

In column 11, lines 35-44, formula (Ea) should appear as follows:

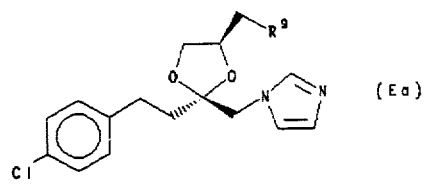

In column 12, insert the following text after line 9 and before line 11:

-- Another preferred process of the invention involves the separation of a compound of formula (Ea):

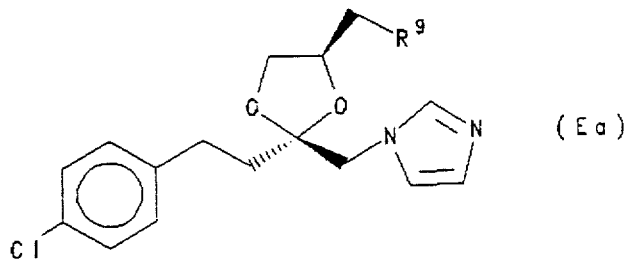

UNITED STATES PATENT AND TRADEMARK OFFICE
CERTIFICATE OF CORRECTION

PATENT NO. : 5,274,108

DATED : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

wherein $R^9$ is tosylate from a mixture of stereoisomers represented by the following formula (E):

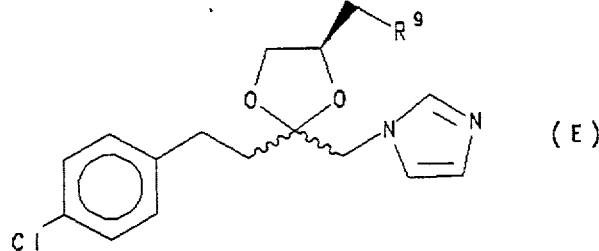

wherein $R^9$ is tosylate; which separation comprises the following steps:

(a) dissolving the mixture of stereoisomers represented by formula (E), as defined above, in a suitable solvent and treating the resulting solution with about 0.8 to about 1.0 molar equivalents of concentrated nitric acid to yield a compound of formula (Eb):

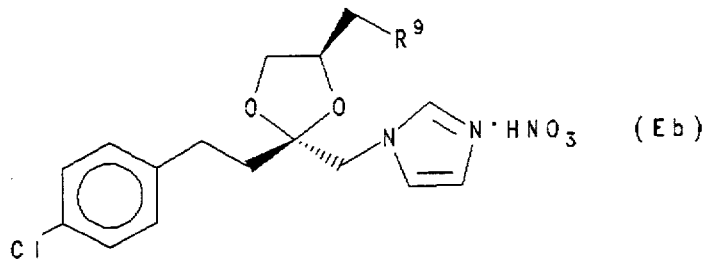

wherein $R^9$ is tosylate as a precipitate;

(b) treating the mother liquor resulting from the preparation of the compound of formula (Eb) with a suitable base and allowing the resulting mixture to crystallize from a suitable solvent to yield a compound of formula (Ea), as defined above. --

UNITED STATES PATENT AND TRADEMARK OFFICE
CERTIFICATE OF CORRECTION

PATENT NO. : 5,274,108

DATED : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In columns 13-14, lines 7-50, <u>Reaction Scheme 2</u>, should appear as follows:

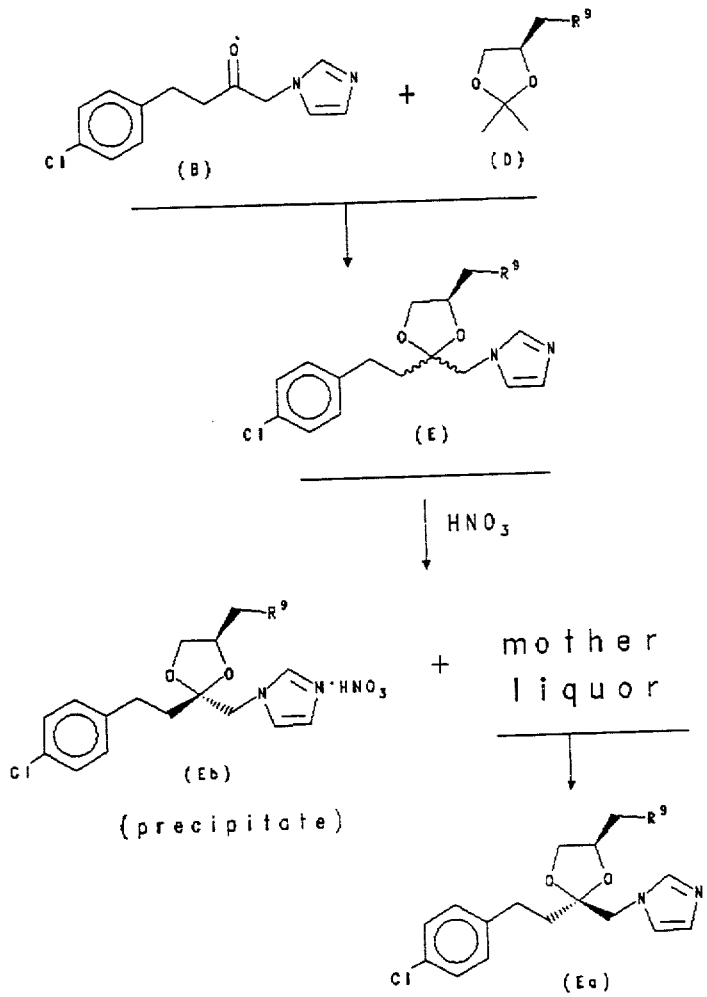

UNITED STATES PATENT AND TRADEMARK OFFICE
CERTIFICATE OF CORRECTION

PATENT NO. : 5,274,108

DATED : December 18, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In column 16, lines 10-41, Reaction Scheme 3, should appear as follows:

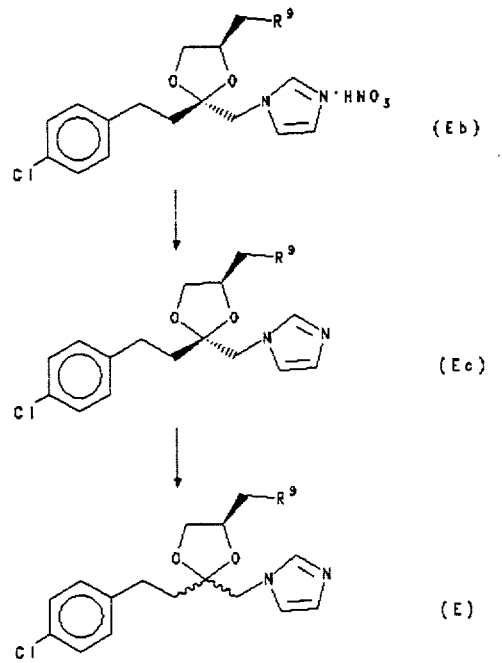

UNITED STATES PATENT AND TRADEMARK OFFICE
CERTIFICATE OF CORRECTION

PATENT NO. : 5,274,108
DATED : December 28, 1993
INVENTOR(S) : Norman H. Dyson, John O. Gardner, Anthony Prince, and Denis J. Kertesz It is certified that error appears in the above-identified patent and that said Letters Patent is hereby corrected as shown below:

In columns 17-18, lines 35-62, <u>Reaction Scheme 4</u>, should appear as follows:

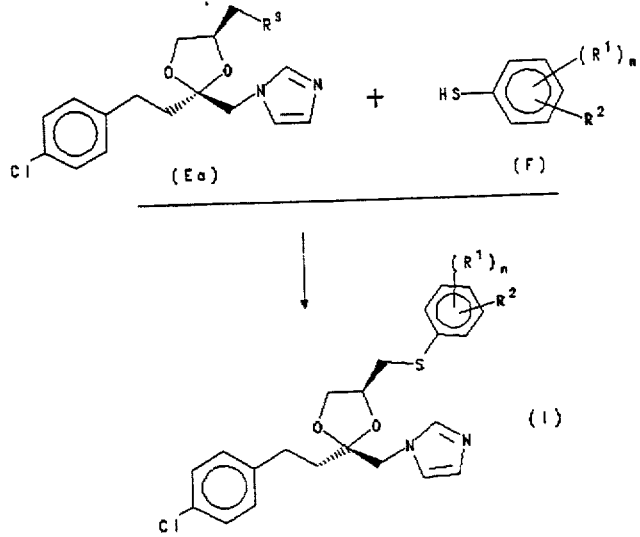

In column 25, Claim 1, lines 25-40, formula (I) should appear as follows:

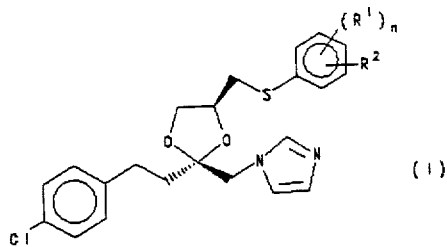

UNITED STATES PATENT AND TRADEMARK OFFICE
CERTIFICATE OF CORRECTION

PATENT NO. : 5,274,108

DATED : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In column 25, Claim 1, lines 57-65, formula (D) should appear as follows:

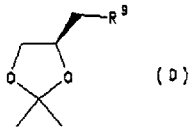

In column 26, Claim 1, lines 1-11, formula (E) should appear as follows:

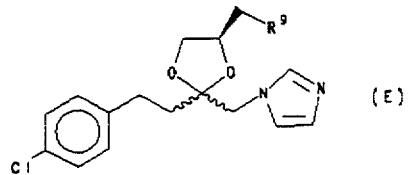

In column 26, Claim 1, lines 18-27, formula (Eb) should appear as follows:

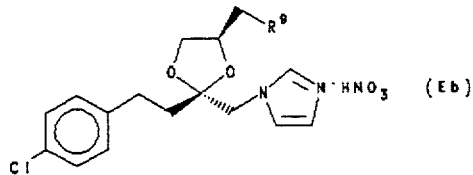

UNITED STATES PATENT AND TRADEMARK OFFICE
CERTIFICATE OF CORRECTION

PATENT NO.  : 5,274,108

DATED       : December 28, 1993

INVENTOR(S) : Norman H. Dyson, John O. Gardner, Anthony Prince, and Denis J. Kertesz It is certified that error appears in the above-identified patent and that said Letters Patent is hereby corrected as shown below:

In column 26, Claim 1, lines 35-44, formula (Ea) should appear as follows:

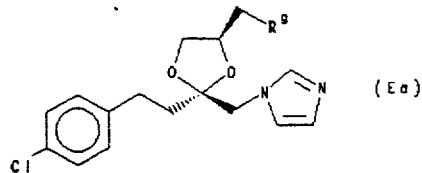

In column 27, Claim 4, lines 7-18, formula (Ec) should appear as follows:

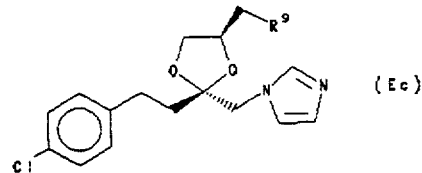

In column 28, Claim 8, lines 1-10, formula (Ea) should appear as follows:

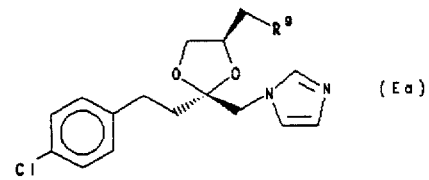

UNITED STATES PATENT AND TRADEMARK OFFICE
CERTIFICATE OF CORRECTION

PATENT NO. : 5,274,108
DATED : December 28, 1993
INVENTOR(S) : Norman H. Dyson, John O. Gardner, Anthony Prince, and Denis J. Kertesz It is certified that error appears in the above-identified patent and that said Letters Patent is hereby corrected as shown below:

In column 28, Claim 8, lines 15-24, formula (E) should appear as follows:

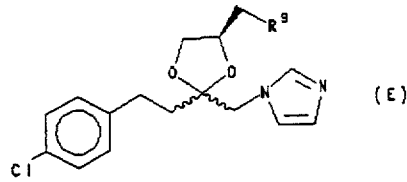

In column 28, Claim 8, lines 32-41, formula (Eb) should appear as follows:

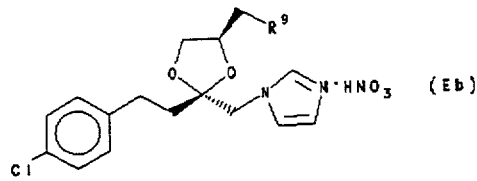

Signed and Sealed this

Twentieth Day of December, 1994

Attest:

BRUCE LEHMAN

Attesting Officer

Commissioner of Patents and Trademarks